United States Patent [19]
Swendson et al.

[11] Patent Number: 5,961,472
[45] Date of Patent: Oct. 5, 1999

[54] CLOSED, ONE-HANDED BLOOD SAMPLING SYSTEM

[75] Inventors: David L. Swendson, Garden Grove; W. Scott Couchman, Irvine; Wesley M. Morris, Corona del Mar; David J. Evans, Irvine, all of Calif.

[73] Assignee: Baxter International Inc., Deerfield, Ill.

[21] Appl. No.: 08/937,670

[22] Filed: Sep. 26, 1997

[51] Int. Cl.⁶ .................................................. A61B 5/00
[52] U.S. Cl. .......................................... 600/573; 600/578
[58] Field of Search ................................ 600/573, 577, 600/578, 579

[56] References Cited

U.S. PATENT DOCUMENTS

| | | | |
|---|---|---|---|
| D. 284,306 | 6/1986 | Moore, Jr. | D24/25 |
| 1,308,954 | 7/1919 | Kennedy | 604/228 |
| 2,233,554 | 3/1941 | Pletcher | 604/208 |
| 2,918,063 | 12/1959 | Tucker | 128/218 |
| 3,572,977 | 3/1971 | Sanz et al. | 417/360 |
| 3,840,011 | 10/1974 | Wright | 128/272 |
| 4,044,757 | 8/1977 | McWhorter et al. | 128/2 A |
| 4,219,055 | 8/1980 | Wright | 141/27 |
| 4,248,225 | 2/1981 | Moore | 128/218 C |
| 4,252,159 | 2/1981 | Maki | 141/27 |
| 4,338,935 | 7/1982 | Wilson | 128/218 |
| 4,434,820 | 3/1984 | Glass | 141/2 |
| 4,639,248 | 1/1987 | Schweblin | 600/578 |
| 4,673,386 | 6/1987 | Gordon | 604/48 |
| 4,711,250 | 12/1987 | Gilbaugh, Jr. et al. | 600/578 |
| 4,778,454 | 10/1988 | LaDow | 604/208 |
| 4,802,645 | 2/1989 | Chiodo | 248/309.1 |
| 4,838,855 | 6/1989 | Lynn | 600/578 |
| 5,071,409 | 12/1991 | Rosenberg | 604/119 |
| 5,115,816 | 5/1992 | Lee | 600/562 |
| 5,135,489 | 8/1992 | Jepson et al. | 604/48 |
| 5,148,811 | 9/1992 | Messinger | 128/673 |
| 5,167,238 | 12/1992 | Newman | 600/573 |
| 5,265,621 | 11/1993 | Simpson et al. | 600/579 |
| 5,301,686 | 4/1994 | Newman | 600/573 |
| 5,324,266 | 6/1994 | Ambrisco et al. | 604/125 |
| 5,374,401 | 12/1994 | von Berg | 422/101 |
| 5,474,546 | 12/1995 | Ambrisco et al. | 604/411 |
| 5,531,672 | 7/1996 | Lynn | 600/578 |
| 5,549,569 | 8/1996 | Lynn et al. | 604/191 |
| 5,582,595 | 12/1996 | Haber et al. | 604/187 |
| 5,643,218 | 7/1997 | Lynn et al. | 604/191 |
| 5,759,160 | 6/1998 | Neese et al. | 600/573 |
| 5,772,608 | 6/1998 | Dhas | 600/578 |

FOREIGN PATENT DOCUMENTS

| | | |
|---|---|---|
| 0 398 354 | 11/1990 | European Pat. Off. . |
| WO 88/01882 | 3/1988 | WIPO . |
| WO 89/04676 | 6/1989 | WIPO . |
| WO 94/06488 | 3/1994 | WIPO . |

*Primary Examiner*—Max Hindenburg
*Assistant Examiner*—Charles Marmor, II
*Attorney, Agent, or Firm*—Guy L. Cumberbatch; Lena I. Vinitskaya

[57] ABSTRACT

A one-handed blood sampling reservoir for an infusion line having a configuration which allows discard fluid to be drawn into the reservoir and then returned to the patient in two squeezing motions. Both drawing and returning steps are performed by squeezing two of a plurality of finger grips provided on the reservoir. The reservoir may include a bracket which enables one-handed operation in either a hand-held or a pole-mounted configurations. In the alternative, the reservoir and finger grips may be formed by telescoped inner and outer housings without a bracket. The reservoir desirably includes a syringe-like body forming a chamber and a plunger/piston assembly reciprocal therein to vary the volume of the chamber. A narrow gap is provided in the chamber open to both inlet and outlet ports when the piston is fully seated to ensure a consistent and minimum flush volume in the chamber. The piston may be spring-loaded against the syringe body to simplify manufacturing by reducing the number of close tolerance parts required. The reservoir is preferably placed within an infusion line having a pressure transducer therein, and the spring loaded piston may be adjustable to vary the dynamic response of the fluid pressure system.

38 Claims, 14 Drawing Sheets

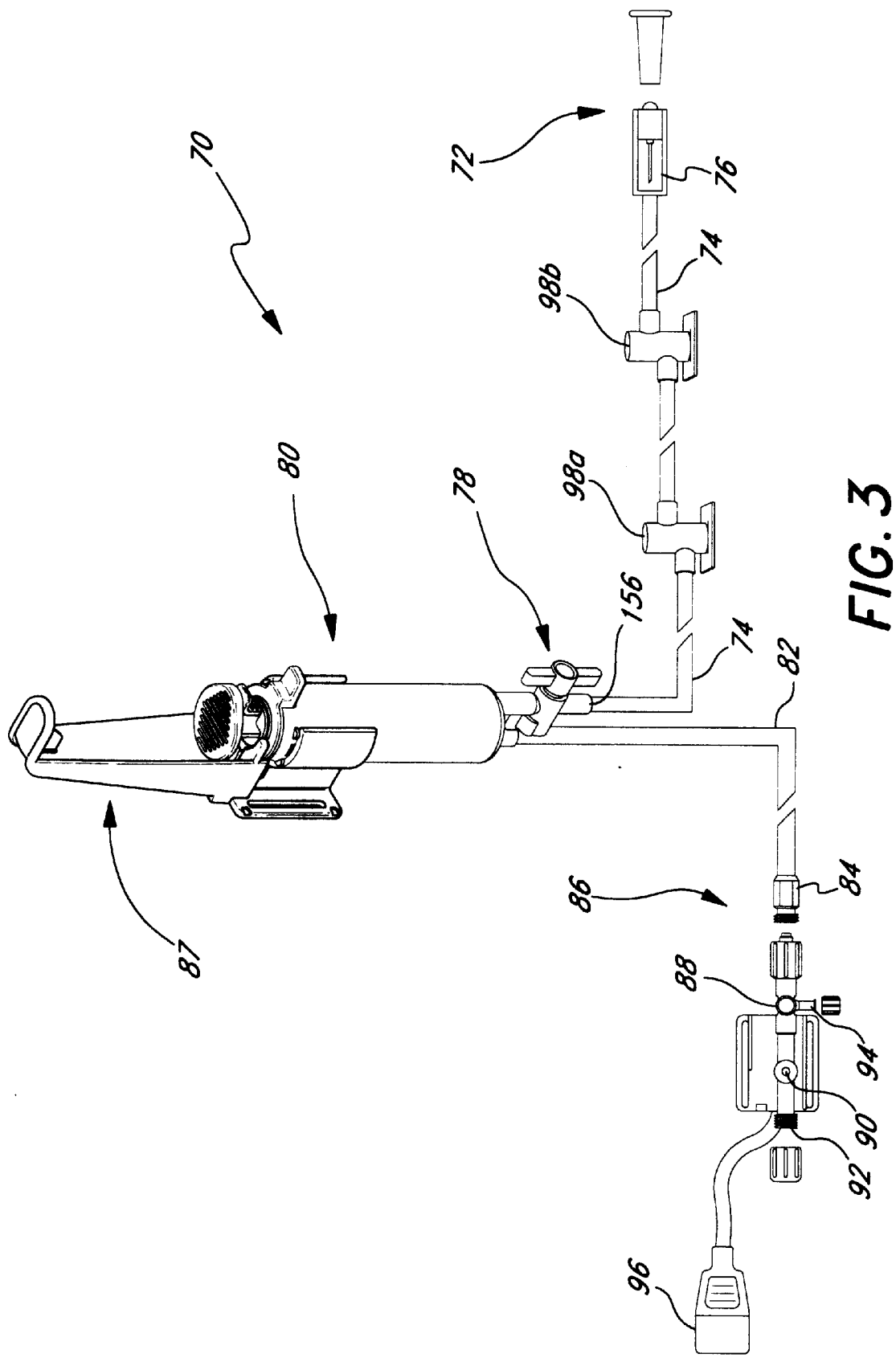

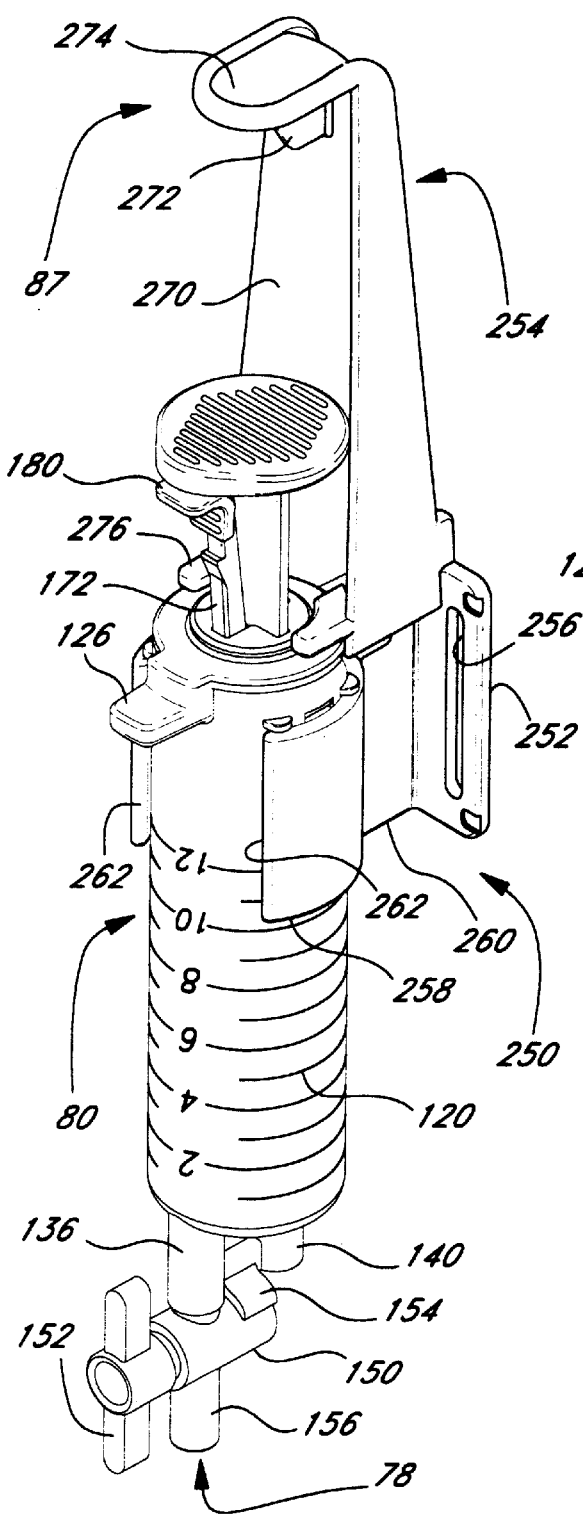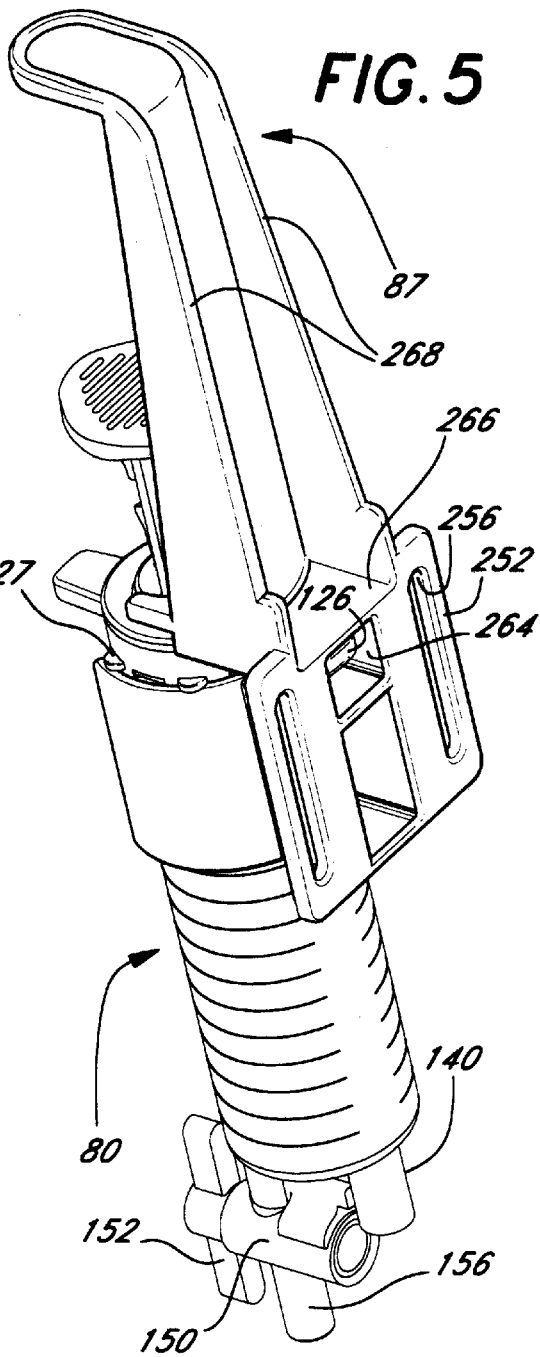

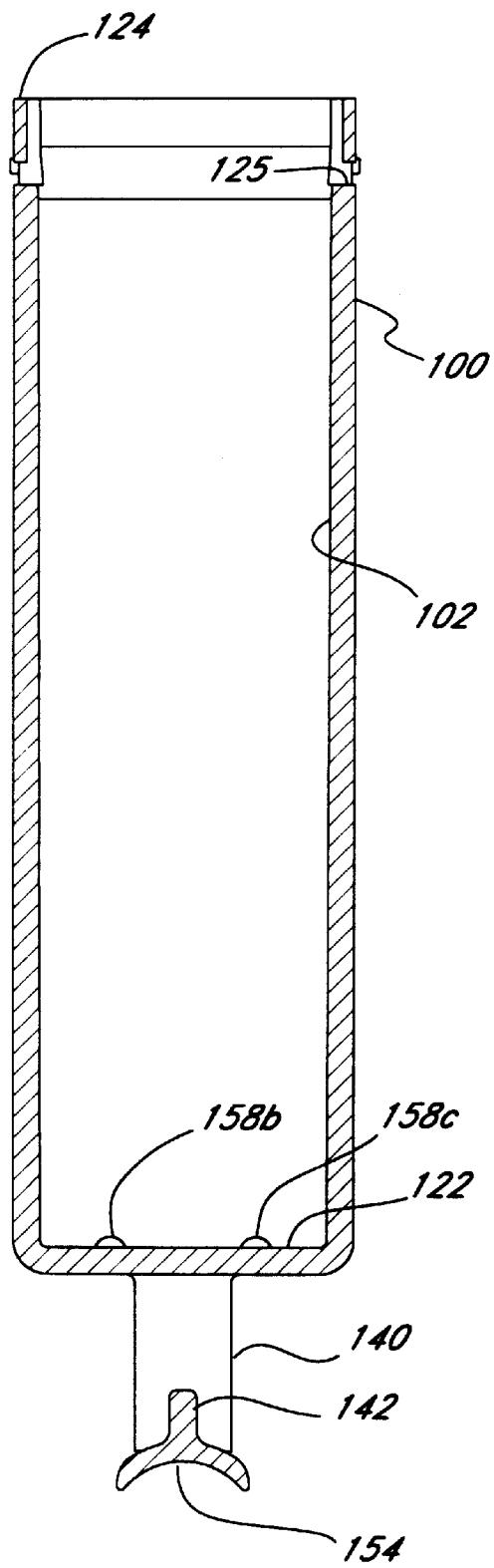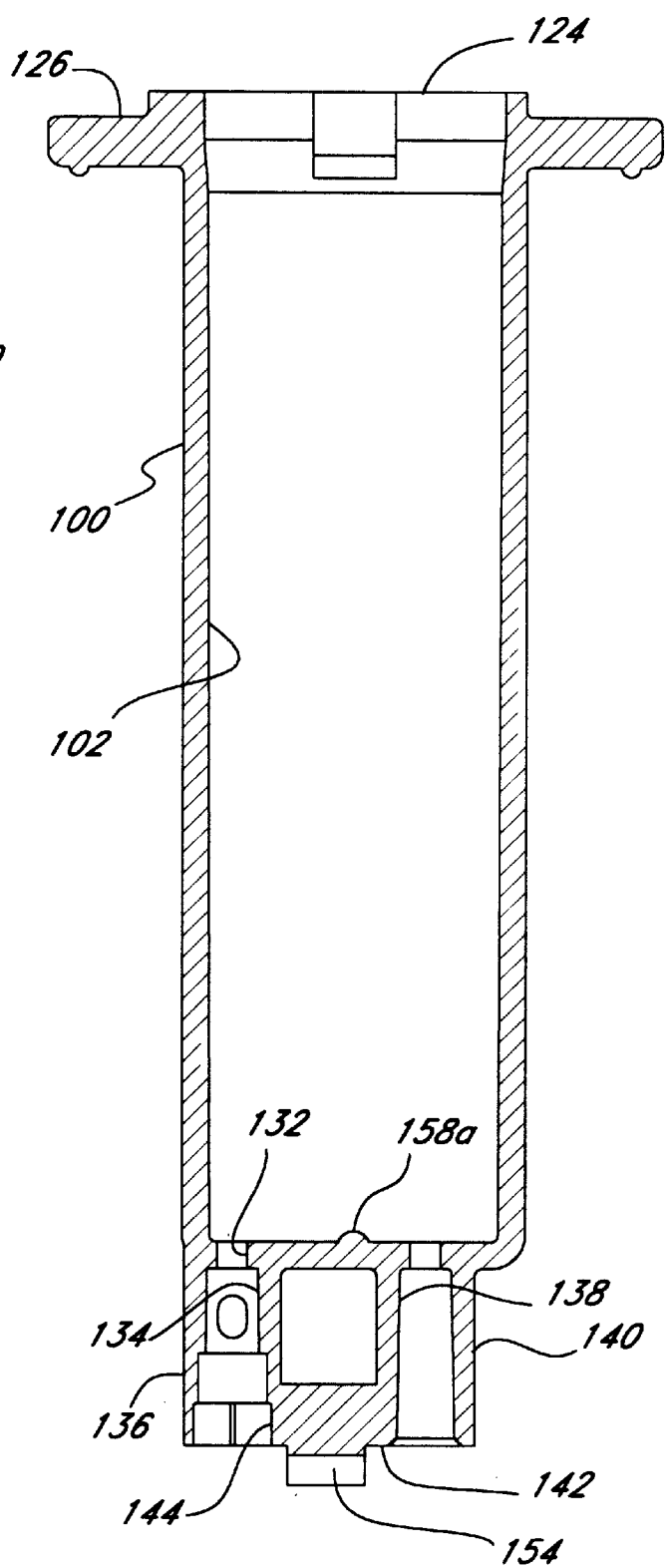

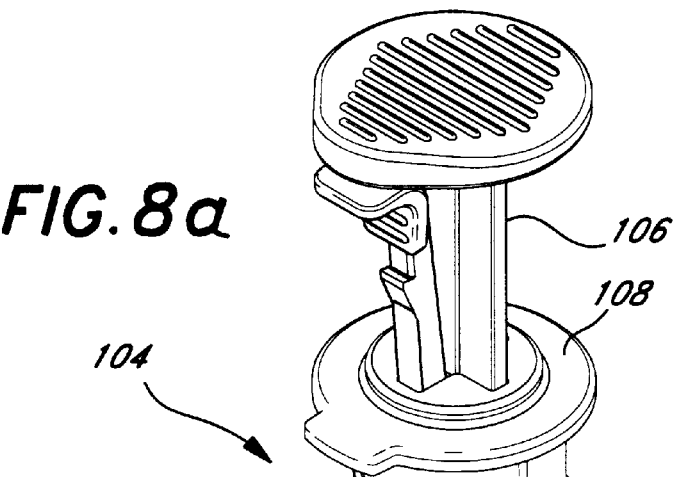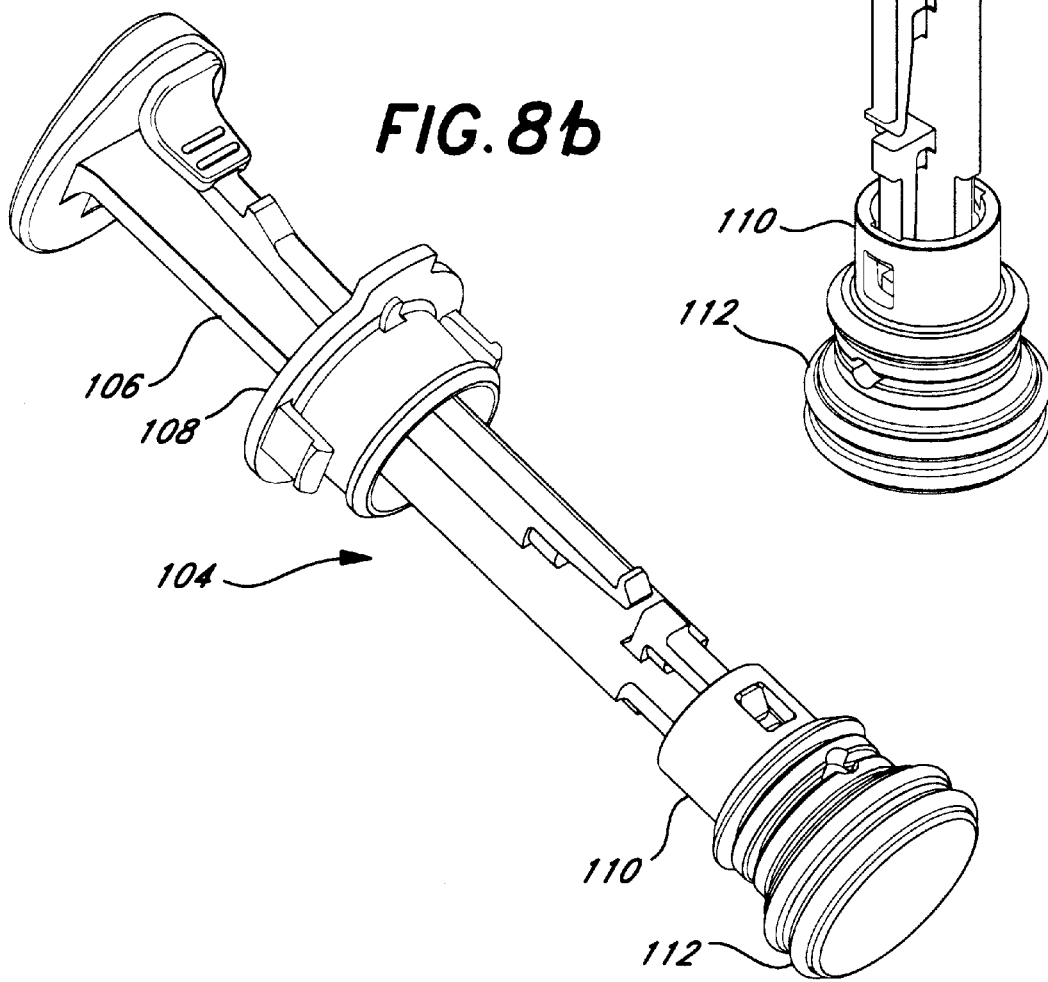

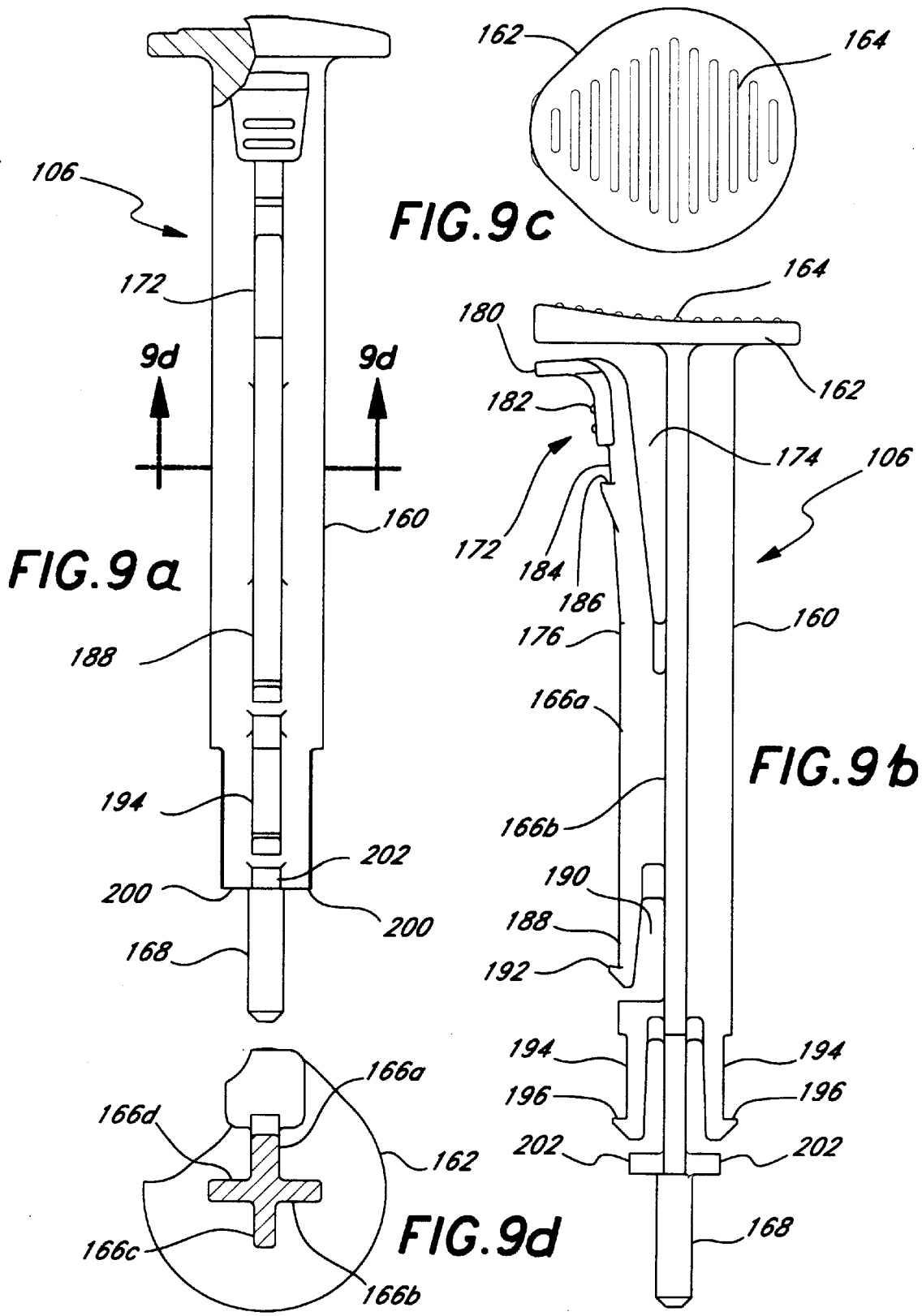

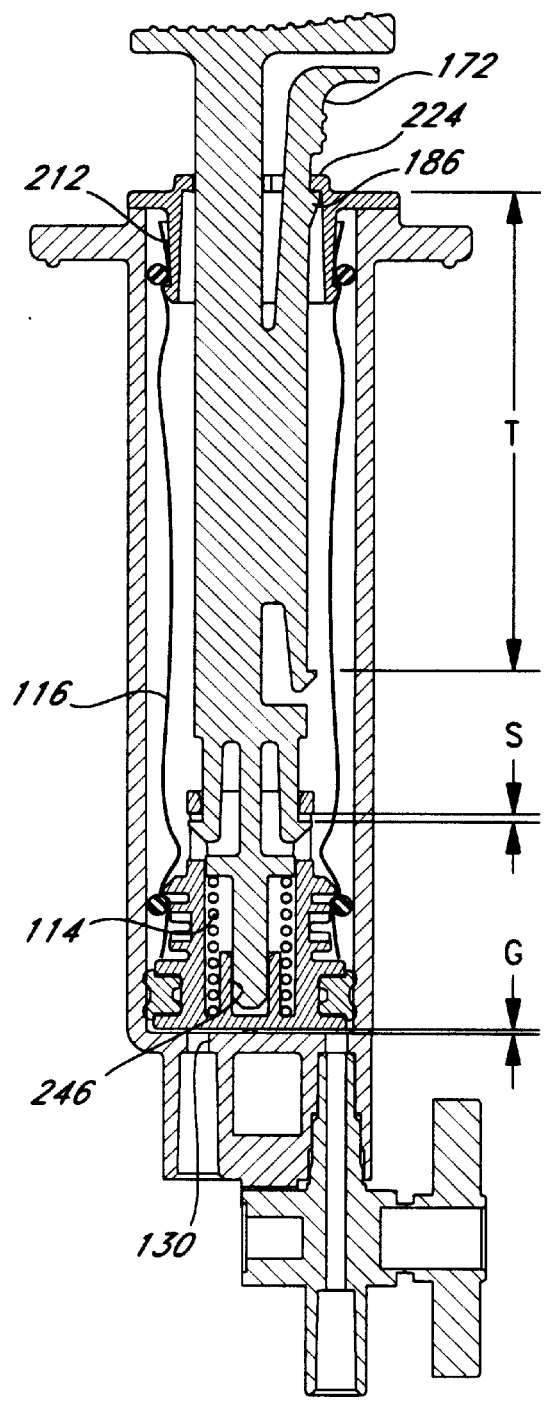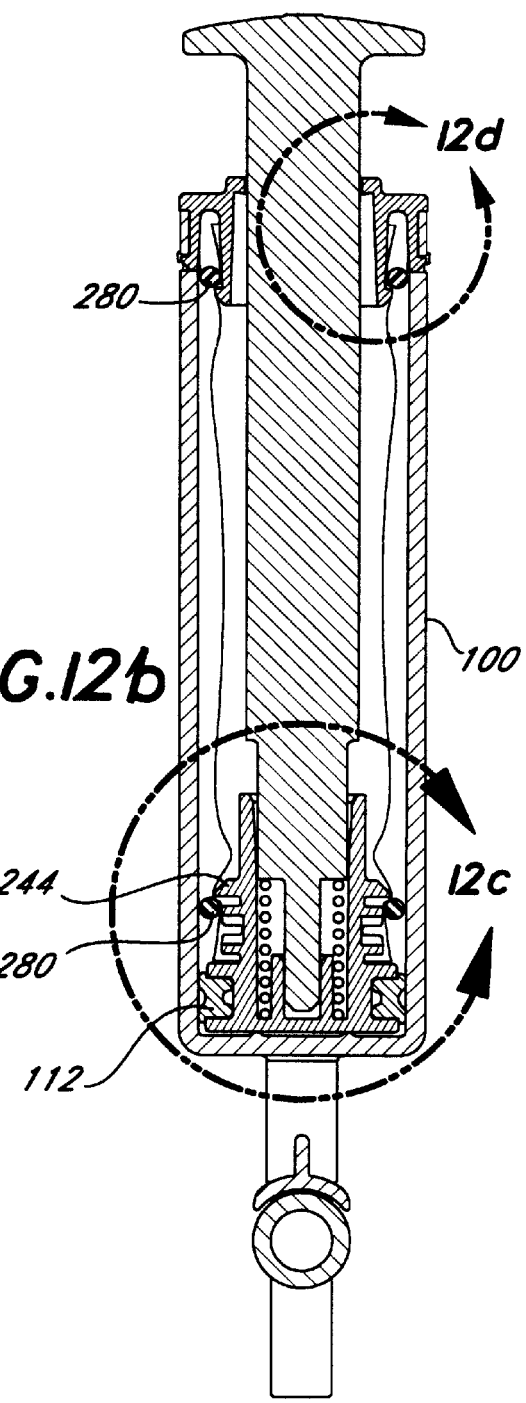

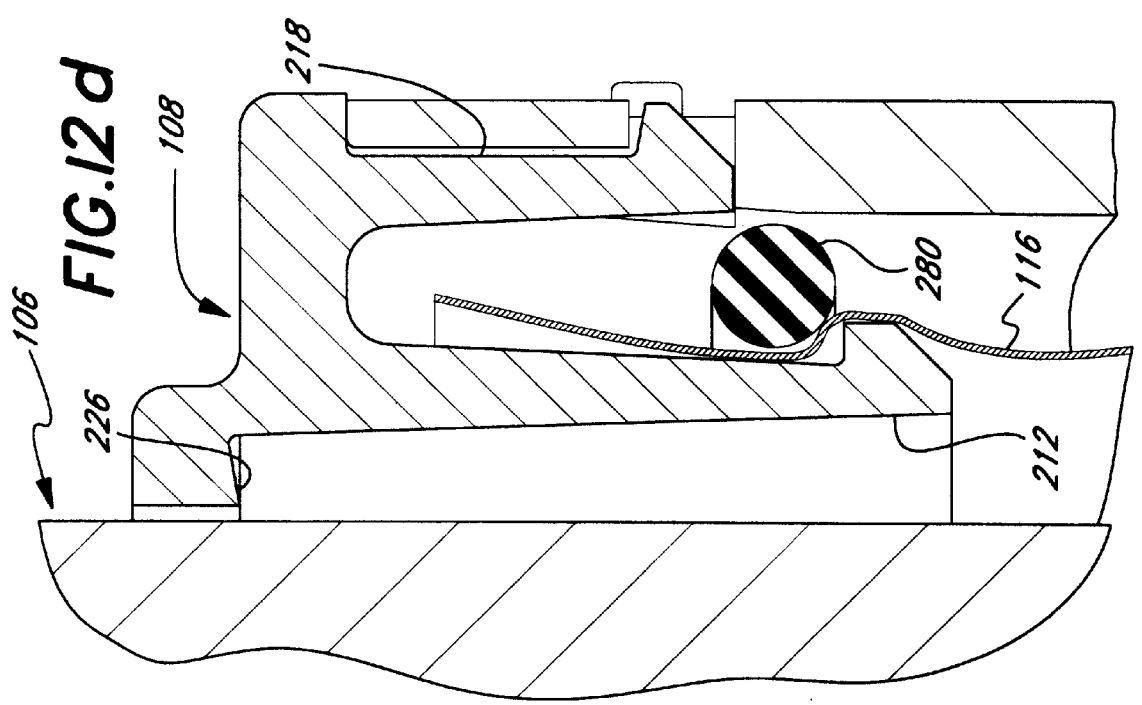
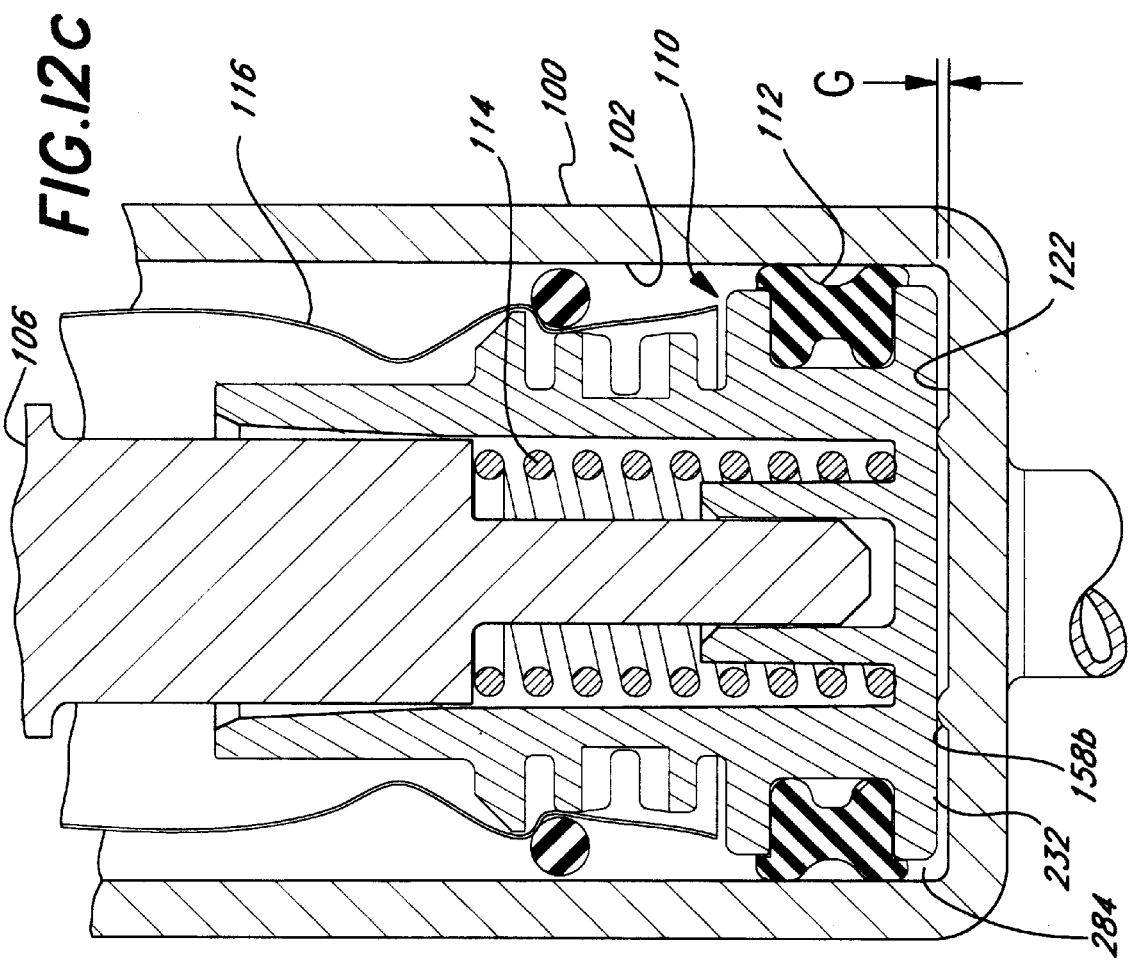

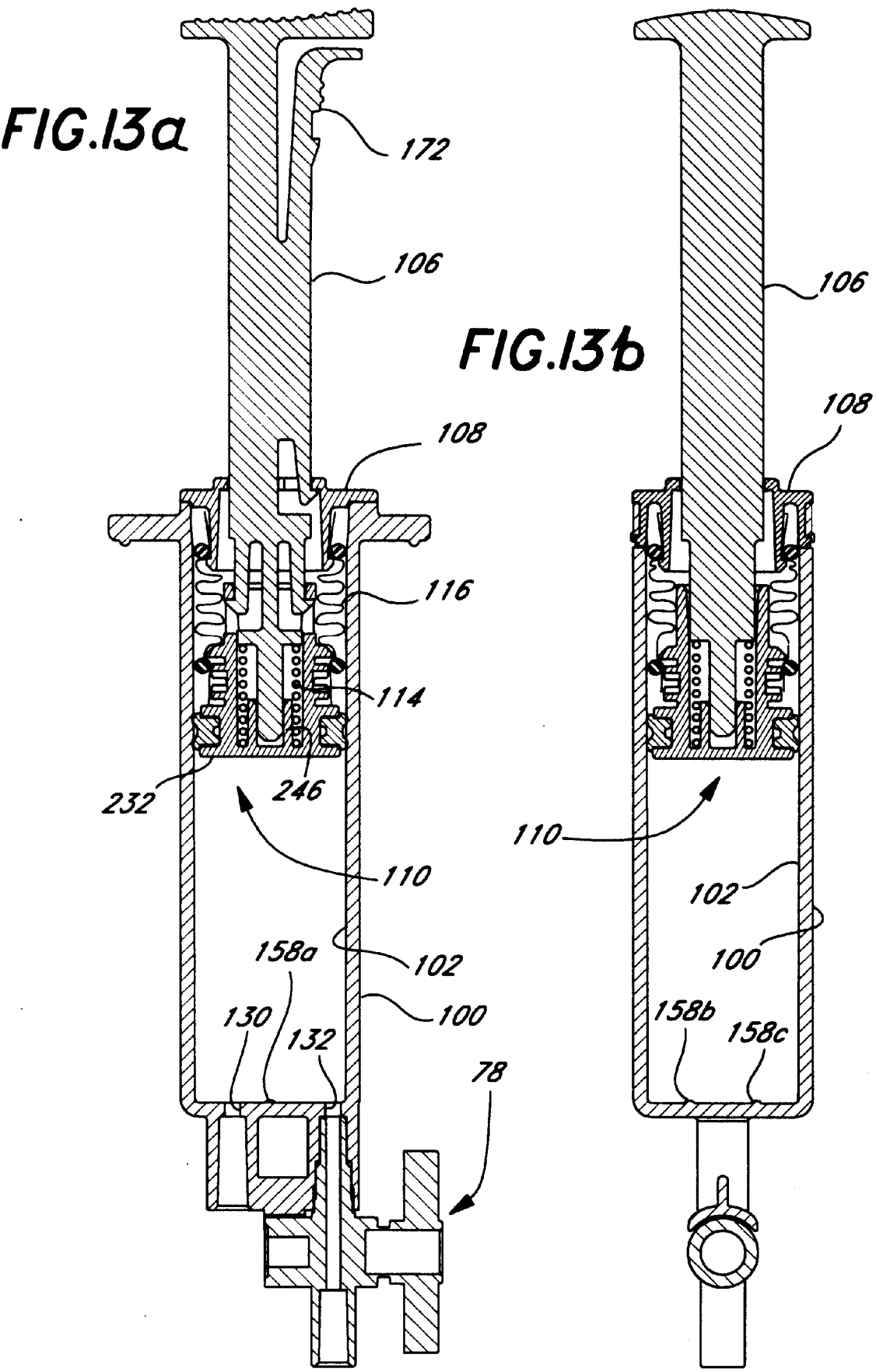

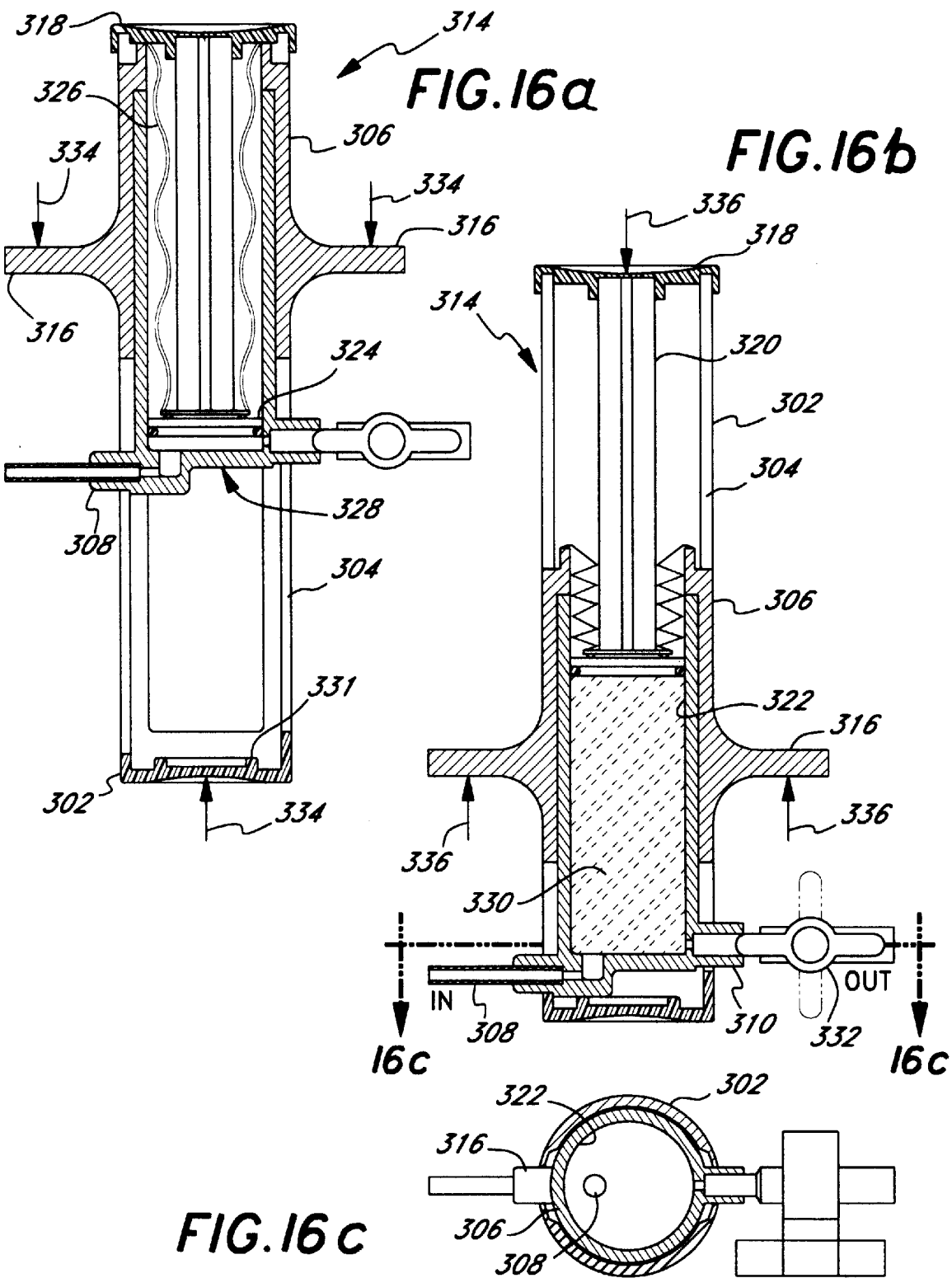

CLOSED, ONE-HANDED BLOOD SAMPLING SYSTEM

FIELD OF THE INVENTION

The present invention relates to blood sampling systems and, in particular, to closed one-handed blood sampling systems and methods of use.

BACKGROUND OF THE INVENTION

In a hospital setting there is always the need to monitor patient health through the evaluation of blood chemistry profile. The simplest method employed in the hospital is to use a syringe carrying a sharpened cannula at one end and insert that cannula into a vein or artery to extract a blood sample from the patient. Patients that are in the critical care units or operating room sometimes require as many as twelve samples a day. Such frequent sampling injections potentially expose the patient to airborne bacteria and viruses which can enter the bloodstream through the opening made by the sharpened cannula. Furthermore, accidental needle sticks of the nurse or technician frequently occur. The problem of infection, accidental needle sticks and ubiquitous danger of contracting viruses such as HIV or hepatitis has prompted the medical field to adopt alternative blood sampling systems.

One way to obtain a blood sample is to draw the blood from a catheter that is already inserted in the patient, either in a central venous line, such as one placed in the right atrium, or in an arterial line. Typically, existing injection sites for arterial or venous drug infusion or pressure monitoring lines are used to take periodic blood samples from the patient. Conventional mechanisms for drawing blood from the lines used for infusion or pressure monitoring utilize a plurality of stopcock mechanisms that preclude flow from the infusion fluid supply or from the pressure column drip supply, while allowing blood to flow from the patient into a collecting syringe connected to a removal port formed in one of the stopcocks. However, stopcocks increase contamination and risk of infection and increase the blood waste. Furthermore, the earliest uses of such sampling sites were with sharpened cannula forced through an elastomeric septum provided in a port in the stopcock housing. Repetitive piercing of the septum at such injection sites were a source of physical damage known as coring or laceration which could shorten the effective life of the injection site. Furthermore, such an apparatus failed to eliminate the danger of the nurse or clinician being stuck by the sharpened cannula.

The next development in sampling systems was to use blunt cannula and slit septums. Although the blunt cannula removed the danger of sticking the nurse or clinician, the possibility of infection by blood borne pathogens remained since the blood at the sampling site and in the syringe was typically under arterial or venous pressure, and in extreme cases could cause a fine spray of blood to contact the user.

Most early systems also required a two-step operation where a first sample of fluid, generally about 5 ml in volume for intensive care environments was withdrawn into the sampling syringe and discarded. This first sample potentially included some of the infusion fluid and thus would be an unreliable blood chemistry measurement sample. After the initial sample had been discharged, the second sample was pure blood from the artery or vein. Aside from the unnecessary loss of blood, the two-sample process potentially introduced undesirable effects relating to such problems as introduction of air into the arterial line and introduction of contaminants into the blood supply. The two-step process also requires substantial effort on the part of the nurses or other clinicians who must draw the blood sample.

In response to the drawbacks associated with earlier sampling systems, closed systems were developed, such as the blood sampler device in U.S. Pat. No. 4,673,386 to Gordon. The Gordon device is shown schematically in FIG. 1 and comprises a piston/chamber device 20 positioned in an infusion line upstream of a sampling port 22. The sampling port 22 includes a slit septum 24 into which a blunt cannula 26 may be inserted for sampling blood therefrom. In use, the piston in the device 20 is retracted to pull fluid from the patient towards the fluid supply and store it in the chamber. Enough fluid is withdrawn into the chamber to pull a pure blood supply past the sampling port 22 so that a syringe 28 can withdraw a usable sample of blood through the blunt cannula 26. In some systems which make use of the Gordon device, such as the Edwards Critical-Care Venous Arterial Blood Management Protection System (VAMP™), a shut-off valve is positioned between the piston/chamber device 20 and sampling port 22 to insure that the syringe 28 does not pull any of the dilute blood or infusion solution from within the chamber. Such closed systems eliminate the problem of needle sticks, and reduce the number of injections into the patient to one for the initial cannula introduction. The process still requires a two-handed operation on the piston/chamber device 20, followed by the two-handed operation of the syringe 28 to obtain the sample of blood.

As mentioned above, blood samples can also be taken from catheter lines used for monitoring blood pressure. The closed system of Gordon shows a pressure transducer 30 placed in the infusion line connected to a monitor 32 which displays the blood pressure. Such pressure lines typically make use of relatively stiff tubing primed with a suitable IV fluid such as saline or 5% dextrose solution as a pressure column. For adults, a bag pressurized with air surrounds an IV fluid supply bag to maintain a constant pressure differential in the line constantly urging fluid toward the patient through a restrictor orifice. The slow drip of IV fluid flushes the line to prevent clotting. The transducer includes a diaphragm exposed to the pressure column on one side and having a device for measuring deflection of the diaphragm on the other. Some transducers such as the TruWave™ Disposable Pressure Transducer available from Baxter Healthcare of Irvine California include a flush device that also can be used for sending transient pressure waves through the line. A Snap-Tab™ device of the TruWave™ is a rubber tab which when pulled and then released sends a square wave through the pressure column which can be used to check the inherent frequency response of the entire system, which includes the tubing and any components attached thereto, such as the sampling ports and temporary fluid storage devices. Proper system frequency response is necessary for reliable blood pressure measurements.

Another closed sampling system manufactured by Abbott Laboratories, and disclosed in U.S. Pat. No. 5,324,266 to Ambrisco, et al., is seen in FIGS. 2A and 2B. This system includes a fluid supply 34 connected through a conduit 36 to a variable flow control device and flush valve 38. The flush valve is connected to the proximal end of a fluid storage mechanism 40 having a piston 42 therein with a hollow interior 44. Infusion fluid from the supply 34 drips through the hollow interior 44 as indicated by arrow 46 and through a vortex inducer element 48 out of the storage mechanism 40. The infusion fluid continues through the line 36 past a shut-off valve 50, a sampling port 52 and finally through a sharpened cannula 54 which has previously been implanted in the patient. When a sample of blood is required, the user grips a lock cap 56 and squeezes the two sides, releasing it from a flange 58. As the cap 56 is withdrawn, the piston 42 creates a vacuum within the fluid storage mechanism 40 pulling blood and residual infusion fluid from the patient into a chamber 60 (FIG. 2B). At this point, the shut-off valve 50 is closed, and a blunt-tipped cannula is used for pulling a sample of blood from a sampling port 52. Although the device in the Ambrisco patent is purportedly easier to use than the Gordon device because of its concentric filling chamber configuration, a two-handed operation to pull fluid within the chamber 60 and a two-handed operation to draw blood from the sampling port 52 are still required.

In view of the foregoing, there is a need for a simplified blood sampling system and method.

SUMMARY OF THE INVENTION

The present invention provides a preferred fluid sampling system comprising a conduit line with a proximal portion adapted to be supplied with a fluid and a distal portion adapted to be in communication with a fluid system of a patient. A reservoir assembly having a variable volume chamber includes an inlet port open to the proximal portion of the conduit line and an outlet port open to the distal portion of the conduit line. A piston is moveable within the chamber to vary the chamber volume. The reservoir assembly has a first pair of pressing surfaces facing away from one another and adapted to displace the piston with respect to the chamber to increase the volume within the chamber, and a second pair of pressing surfaces facing away from one another and adapted to displace the piston with respect to the chamber to decrease the volume within the chamber, wherein fluid may be drawn into the chamber and expelled therefrom upon actuation of the first and second pair of pressing surfaces, respectively. The reservoir assembly may comprise a syringe-like device and include a bracket for mounting the assembly to an external support, the syringe-like device being attached to the mounting bracket, wherein one of the first pair of pressing surfaces is on the bracket. The reservoir assembly may include a body defining the chamber within and a plunger assembly comprising the piston on a first end and a plunger on a second end extending outside of the body, wherein the plunger defines the other of the first pair of pressing surfaces for cooperating with the one on the bracket. The plunger preferably defines one of the second pair of pressing surfaces, and the body includes a generally radially outwardly extending member which defines the other of the second pair of pressing surfaces for cooperating with the one on the plunger.

The present invention also provides a preferred method of sampling fluid using a reservoir assembly and a sampling port located in a line attached to a catheter in communication with a fluid system of a patient. The method comprises squeezing a first pair of pressing surfaces on the reservoir assembly, the first pair of pressing surfaces facing in opposite directions, so as to displace a piston within a variable volume chamber defined within the reservoir assembly and withdraw a fluid from the patient past the sampling port and into the chamber. Fluid is sampled from the sampling port, and a second pair of pressing surfaces facing in opposite directions on the reservoir assembly are squeezed to displace a piston within the variable volume chamber and infuse fluid from the chamber past the sampling port and into the patient. The reservoir assembly may include a syringe-like device having an axis wherein squeezing the first or second pair of pressing surfaces displaces the piston axially to respectively increase or decrease the chamber volume. The reservoir assembly may include the syringe-like device and a bracket for mounting the assembly to an external support, with the syringe-like device attached to the mounting bracket, wherein one of the first pair of pressing surfaces is on the bracket. The mounting bracket may have a retaining portion and the syringe-like device may have a body defining the chamber within, with the body being received in the retaining portion and held from axial movement with respect thereto. In a preferred form, a plunger assembly is provided comprising the piston on a first end and a plunger on a second end extending outside of the body, wherein the plunger defines the other of the first pair of pressing surfaces for cooperating with the one on the mounting bracket. Additionally, the plunger may define one of the second pair of pressing surfaces, and the body may include a generally radially outwardly extending member which defines the other of the second pair of pressing surfaces for cooperating with the one on the plunger.

In another preferred embodiment, a reservoir for use in a fluid sampling system is provided. The reservoir comprises: a reservoir body defining a chamber within; a piston having a piston wall facing the chamber and displaceable within the body from a first position to a second position to vary the volume of the chamber; a fluid inlet port and a fluid outlet port open to the chamber; structure on either the body or the piston which maintains a minimum gap between the piston wall and the body when the piston is in the first position, the gap defining a volume to which the inlet and outlet ports communication to allow fluid to flow therebetween; and a biasing member which urges the piston wall into the first position.

The present invention also provides another preferred method of flushing a reservoir used in a sampling system. The method comprises the steps of providing a reservoir having a chamber and a displaceable piston having a piston wall facing the chamber and displaceable within the body to vary the volume of the chamber, connecting a proximal portion of tubing between a source of flushing fluid and an inlet to the variable volume chamber, connecting a distal portion of tubing between a fluid system of a patient and an outlet to the variable volume chamber, biasing the piston into a first position within the variable volume chamber with the piston wall adjacent the inlet and outlet ports, and maintaining a minimum gap between the piston wall and the chamber when the piston is in the first position with structure on either the chamber or the piston, the gap defining a volume to which the inlet and outlet ports communicate and allow fluid to flow from the proximal portion of tubing to the distal portion of tubing.

In another preferred embodiment, a reservoir for use in a fluid sampling system is provided. The reservoir comprises a reservoir body defining a variable volume chamber within, the body having a peripheral wall and a bottom wall. A fluid inlet port extends perpendicularly through the bottom wall of the body and opens to the chamber. A fluid outlet port also opens to the chamber. A piston is displaceable within the body from a first position adjacent the bottom wall to a second position spaced farther away from the bottom wall to increase the volume of the chamber. The piston has a pressure surface which is spaced from the bottom wall to form a narrow gap therebetween when the pistonis in the first position, with the fluid inlet and outlet ports being open to the gap. Finally, a seal surrounds the pressure surface and provides a fluid-tight seal between the piston against the peripheral wall of the chamber. Fluid entering the chamber through the inlet port when the piston is in the first position is directed generally in a 360° sheet across the bottom wall and toward the peripheral wall of the chamber.

Further objects and advantages of the present invention shall become apparent to those skilled in the art upon reading and understanding the following detailed description of a presently preferred embodiment of the invention.

BRIEF DESCRIPTION OF THE DRAWINGS

FIG. 3 is a schematic diagram of a blood sampling system of the present invention incorporating an improved blood sampling reservoir;

FIGS. 4 and 5 are front and rear perspective views of the blood sampling reservoir used in the system of FIG. 3;

FIG. 7a is a cross-sectional view of the reservoir main body taken along line 7a—7a of FIG. 6c;

FIG. 7b is a cross-sectional view of the reservoir main body taken along line 7b—7b of FIG. 6d;

FIGS. 8a and 8b are top and bottom perspective views of a plunger assembly of the reservoir of FIGS. 4 and 5

FIGS. 9a and 9b are front and side elevational views of a plunger component of the reservoir of FIGS. 4 and 5;

FIGS. 9c is a top plan view of the plunger;

FIGS. 9d is a cross-sectional view of the plunger along line 9d—9d of FIG. 9a;

FIGS. 12a and 12b are side and front cross-sectional views of the assembled reservoir of FIGS. 4 and 5 showing a plunger assembly fully seated within the main body;

FIG. 12c is an enlarged portion of the reservoir within the circle 12c—12c of FIG. 12b;

FIG. 12d is an enlarged portion of the reservoir within the circle 12d—12d of FIG. 12b;

FIGS. 13a and 13b are side and front cross-sectional views of the assembled reservoir showing the plunger assembly fully retracted within the main body;

FIGS. 16a, 16b and 16c are cross-sectional views of a blood sampling reservoir similar to that shown in FIG. 15.

DESCRIPTION OF THE PREFERRED EMBODIMENTS

Figure 1:
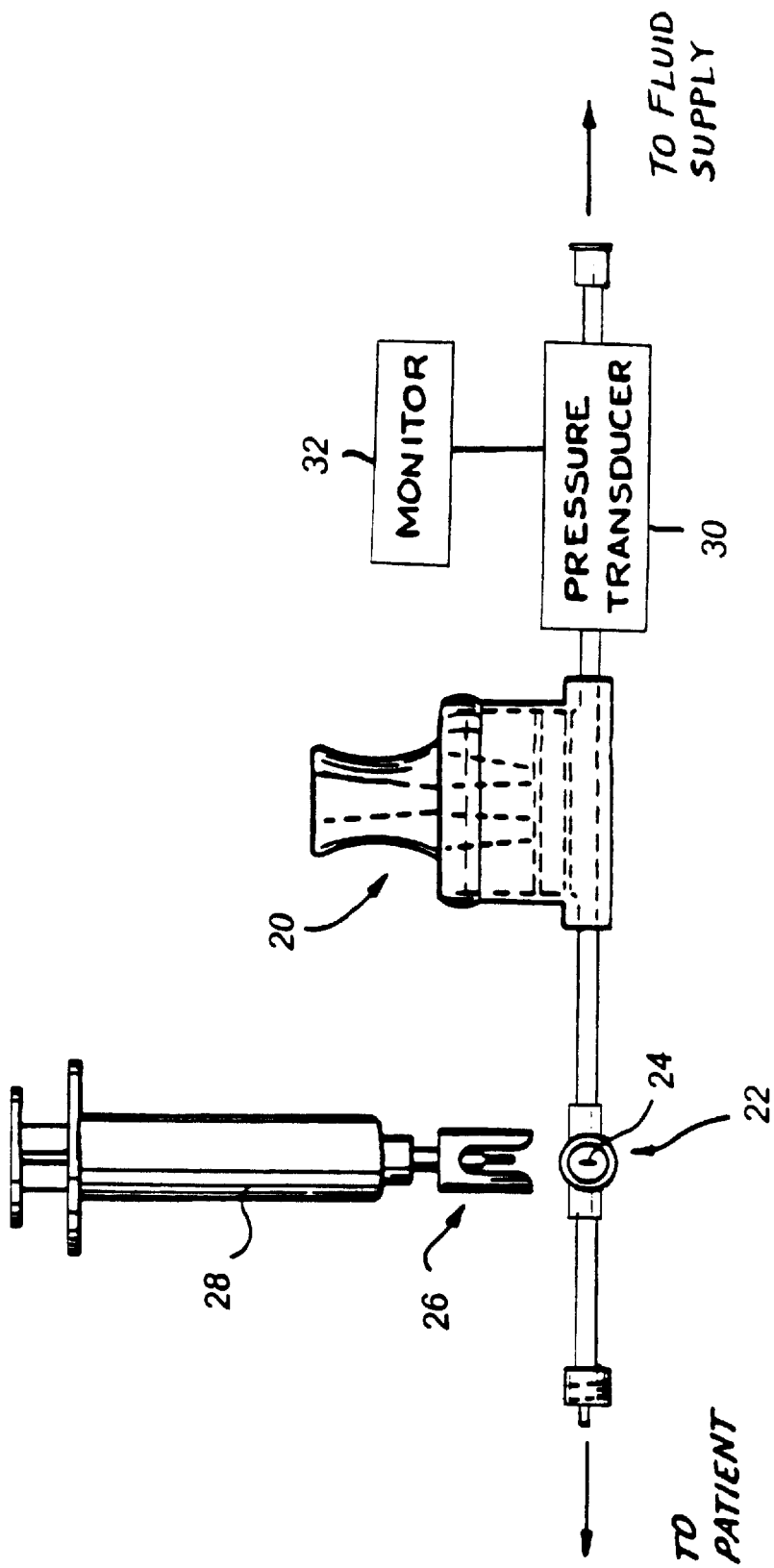
FIG. 1 is a schematic diagram of a blood sampling system of the prior art.
Figures 2A, 2B:
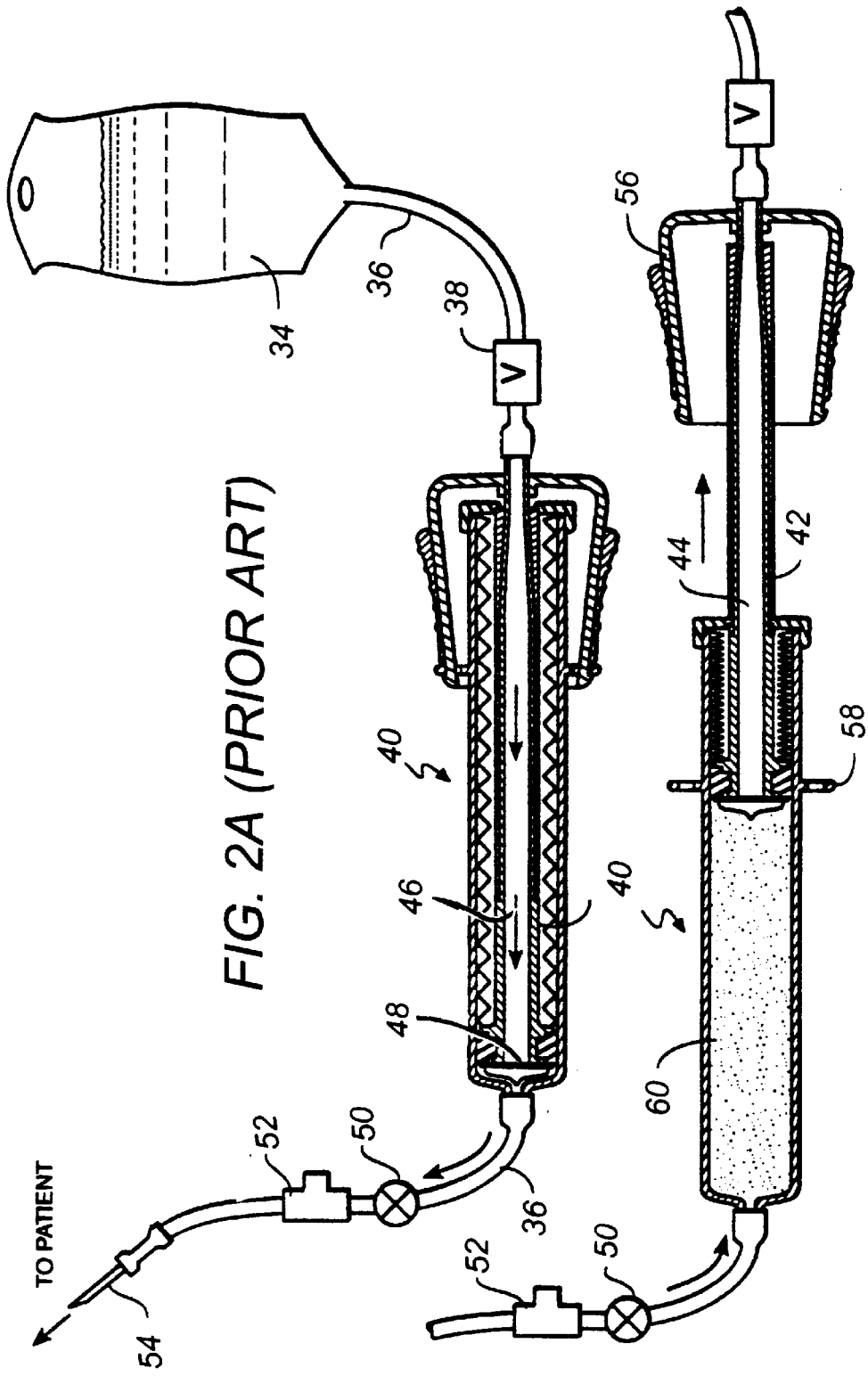
FIGS. 2A and 2B are schematic cross-sectional views of another prior art blood sampling system.

The present invention comprises an improved, closed, one-handed blood sampling system especially useful for the operating room or critical care unit (CCU). This system provides flexibility in allowing a blood withdrawal reservoir to be mounted to a bracket or removed from the bracket, and the operation of the reservoir requires minimal effort. In one form, the reservoir forms a part of a pressure monitoring system and includes a consistently open channel for flow therethrough to flush surfaces in contact with blood. An inlet and outlet port to the reservoir further insures good flushing of the channel therethrough. In another advantageous feature, the blood sampling system enables adjustment of the frequency response of the pressure column to provide clearer and more accurate readings from a pressure monitoring transducer within the system. These and other advantages will be apparent from the detailed description below.

Sampling System

FIG. 3 schematically illustrates a blood sampling system 70 of the present invention. System 70 comprises a distal end 72 terminating in a male luer connector 76 for attaching to a female luer connector (not shown) of an injection site, or other conduit leading to the patient. A first tubing line 74 extends between the distal end 72 and a one-way stopcock 78. The stopcock 78 is preferable rigidly attached to the bottom end of a reservoir 80. A second tubing line 82 extends from the reservoir 80 in a proximal direction and terminates in a female luer connector 84 at a proximal end 86 of the blood sampling system 70. The reservoir 80 is removably mounted to a bracket 87 which, in turn, may be secured to a conventional pole support with the reservoir in a vertical orientation.

As mentioned above, the blood sampling system 70 preferably forms a portion of a pressure monitoring system, and the female luer connector 84 is attached to a T-junction 88 which in turn has one port connected to a pressure transducer 90, such as a TruWave™ Disposable Pressure Transducer available from Baxter Healthcare of Irvine California. A supply of flush solution (not shown) is connected to a flush port 92 of the transducer 90. In addition, an infusion fluid supply (not shown) may be provided in communication with an infusion port 94 of the T-junction 88. The pressure transducer 90 is thus placed in fluid communication with the arterial or venous system of the patient through the lines 74 and 82, and preferably includes a coaxial cable and plug 96 to connect to a display monitor.

The sampling system 70 further comprises a pair of sampling sites 98a and 98b. The sampling sites 98 each desirably define Z-shaped passages therein to induce turbulence and enhance blood clearing from around a pre-slit septum (not numbered). With this configuration, a minimal amount of flush volume is needed to clear the line after sampling. The septum preferably comprises a latex disc which accepts a blunt cannula and reseals after each sample is drawn, reducing the potential for contamination and eliminating the danger of needle sticks. Such sampling site is described in U.S. Pat. No. 5,135,489 to Jepson, et al., which is hereby expressly incorporated by reference.

Reservoir

Figure 15:
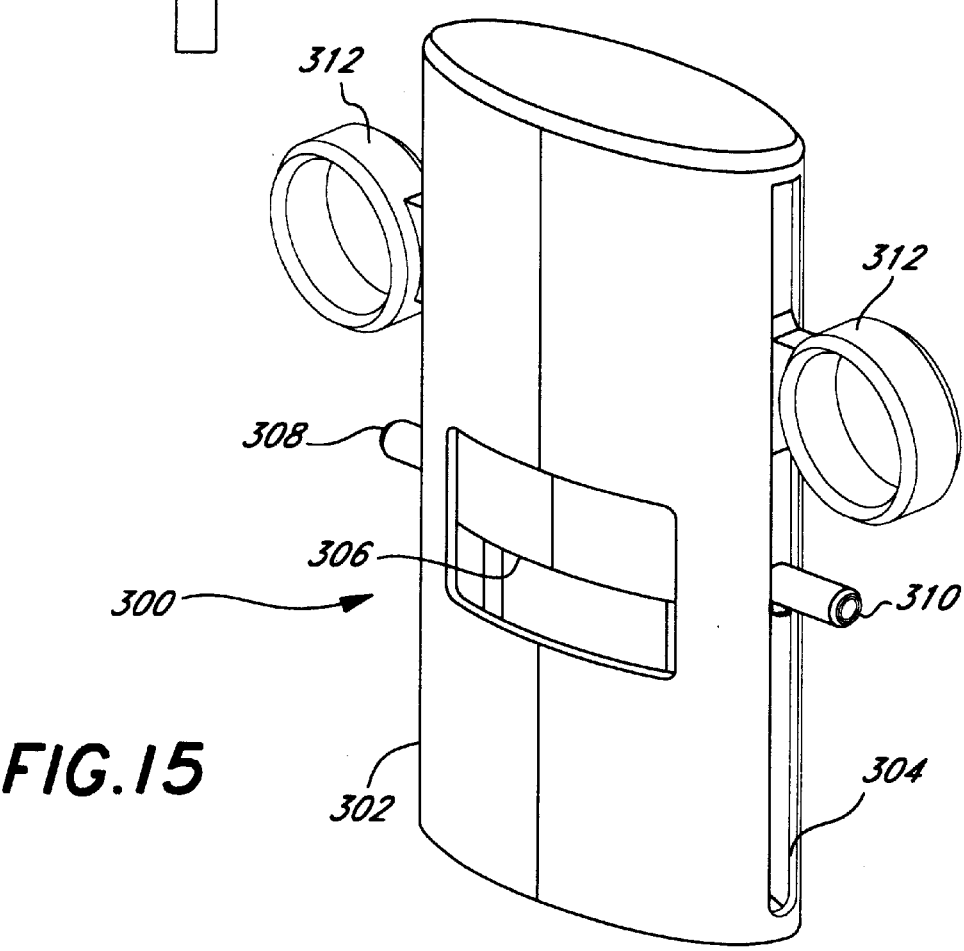
FIG. 15 is perspective view of an alternative blood sampling reservoir of the present invention.

FIGS. 4–5 illustrate one embodiment of a blood sampling reservoir 80 of the present invention attached to the bracket 87. The reservoir 80 is desirably a syringe-type variable volume chamber for withdrawing fluid from the distal end 72 of the system 70. In addition, the reservoir 80 includes a constantly open flow channel for passage of flushing fluid from the proximal end 86 to the distal end 72. Finally, the reservoir 80 has the capacity to reinfuse blood and other fluids drawn into the reservoir during the sampling operation, thus eliminating a waste volume. The entire sampling system 70 is thus closed as the "priming" volume ensuring a pure sample of blood at the sites 98a and 98b remains within the system 70 and is reinfused into the patient. It will be understood by those of skill in the art that the syringe-type embodiment 80 shown in FIGS. 4–5 is only exemplary and other configurations may be designed to adequately perform the inventive functions of the present application. For example, the reservoir 300 shown in FIG. 15 is a further embodiment which does not include a separable bracket for one-handed operation. In short, the presently preferred embodiment of FIGS. 4–5 should be considered exemplary and not necessarily limiting.

Plunger Assembly

As seen in cross-section in FIGS. 7a and 7b, the reservoir 80 comprises an outer body 100 defining an inner cylindrical chamber 102 which receives a plunger assembly 104. With reference to FIGS. 8a and 8b, the plunger assembly 104 comprises, from top to bottom, a plunger 106, a cap 108 adapted to attach to an open upper end of the chamber 102, a piston 110, and a seal 112. The reservoir 80 is generally elongated along an axis which will be described for orientation purposes as vertical with the cap 108 on an upper end thereof. In use, however, the reservoir 80 will often be inverted, as described below. The reservoir body 100, plunger 106, cap 108 and piston 110 are preferably molded biocompatible polycarbonate parts, while the seal 112 is preferably a silicone elastomer. Other materials may be suitable, however.

The assembled plunger assembly 104 reciprocates vertically within the chamber 102 and the seal 112 is sized to provide a fluid-tight, displaceable gasket or wiper at the bottom of the plunger assembly 104. With reference to FIG. 12a, the plunger assembly further includes a spring 114 placed in compression between the plunger 106 and the piston 110, and a contamination shield 116 surrounding a major portion of the plunger assembly 104. These components will be described in greater detail below.

Reservoir Body

Figure 6B:
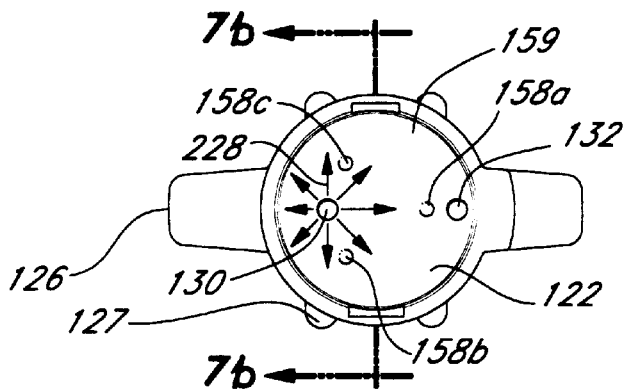
FIGS. 6b and 6c are top and bottom plan views of the reservoir main body.
Figure 6A:
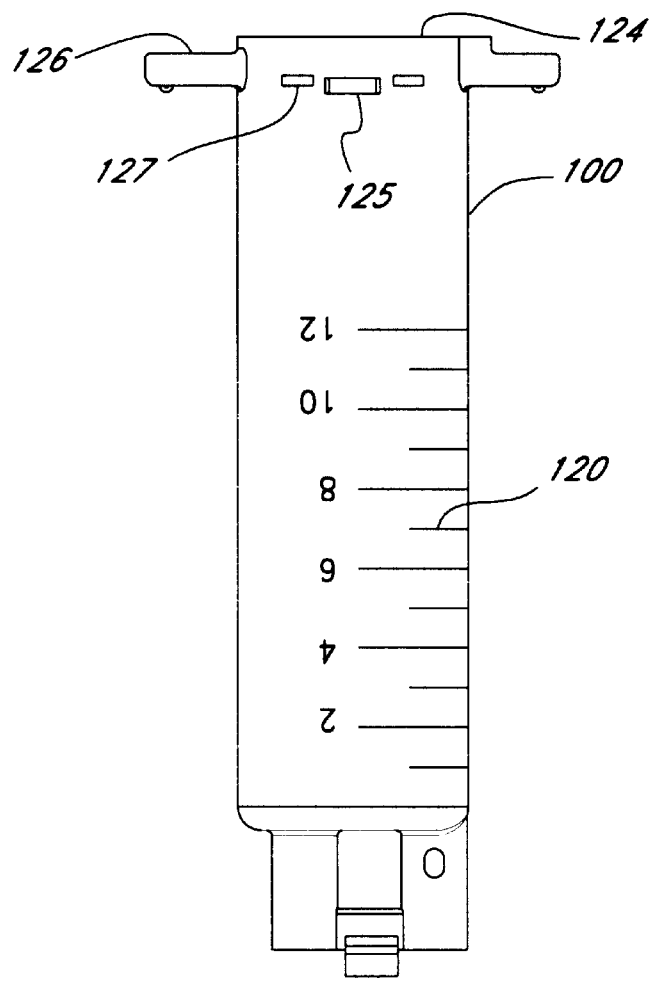
FIG. 6a is a side elevational view of a main body of the reservoir of FIGS. 4 and 5.
Figure 6C:
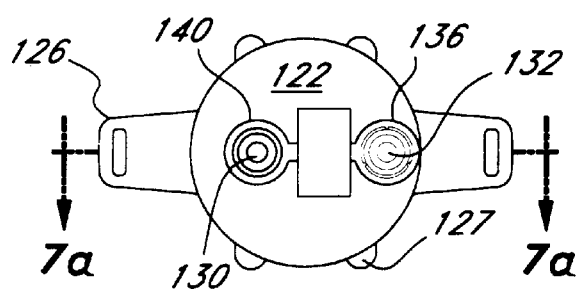

As best seen in FIGS. 6 and 7, the exterior of the body 100 is preferably cylindrical and includes gradations 120 with corresponding numeric markings indicating a volume of fluid within the chamber 102. In this respect, the body 100 includes a circular, planar bottom wall 122 and an upper mouth 124 (which receives the cap 108). A pair of diametrically opposed slots 125 are formed near the top of the body 100 for securing the cap 108 over the mouth 124. A pair of outwardly extending finger grips or wings 126 is provided proximate the open mouth 124. Additionally, the body 100 includes a pair of exterior tabs 127 positioned on both sides of each slot 125, for interacting with the bracket 87. In one embodiment, the body 100 comprises a constant diameter cylinder from the bottom wall 122 to the open mouth 124 having an inner diameter of approximately 0.75 inch (1.90 cm) and a height of approximately 3 inches (7.6 cm). In this embodiment, the chamber 102 has a volume sufficient to withdraw at least 12cc of fluid, which is typically sufficient for operating room sampling procedures. In other embodiments, the reservoir 80 may be provided only for CCU applications and may include a smaller drawing volume.

Below the bottom wall 122 of the body 100 are provided fluid inlet and outlet ports to the chamber 102, as best seen in FIGS. 6b and 7a. More particularly, looking into the top of the chamber 102 in FIG. 6b, an inlet port 130 is formed as an aperture in the bottom wall 122 at a location approximately halfway between the periphery and center of the chamber. An outlet port 132 of preferably the same diameter as the inlet port 130 is provided proximate the periphery of chamber 102. As used herein, the term inlet refers to the direction fluid flows from a source of flush solution to the patient, but it will be understood by those of skill in the art that in the sampling operation fluid actually flows in through the outlet port 132. The outlet port 132 opens to a tubing lumen 134 defined within a rigid cylinder 136. Likewise, the inlet port 130 opens to a lumen 138 defined by a rigid cylinder 140. The cylinders 136 and 140 depend downwardly from the bottom wall 122 approximately the same distance and are connected by a web 142. The web 142 reinforces the cylinders 136 and 140 to prevent accidental breakage thereto. The lumen 134 has a first diameter and opens to a wider lumen 144. Significantly, the lumen 138 leading to the inlet port 130 is oriented perpendicularly with respect to the bottom wall 122 to enhance a reservoir flushing operation described below.

The stepped lumens 134 and 144 receive a nipple of the stopcock valve 78, seen in FIGS. 4 and 5. Stopcock valve 78 typically comprises a cylindrical main body 150 defining a housing within which a stopcock valve 152 rotates. In the present embodiment, an arcuate saddle 154 shaped to receive the cylindrical main body 150 of the stopcock valve 78 is rigidly attached to the lower end of the web 142. Desirably, the stepped diameter stopcock nipple is glued in place within the lumens 134 and 144. The end of the valve body 150 opposite from the nipple comprises a female connector tube 156 for receiving the first tubing line 74, as seen in FIG. 3. Likewise, the tubing lumen 138 for the inlet port 130 receives the second tubing line 82. The tubing lines 74 and 82 can be glued in place for security.

The bottom wall 122 further includes one or more upstanding protrusions or bumps 158a, 158b, and 158c extending into the chamber 102 which interact with the piston 110 to space it from the bottom wall, as will be explained below, and ensure a consistent and minimal flush volume in the reservoir 80. There are desirably at least three bumps 158a,b,c evenly spaced about a circle positioned slightly off center in the bottom wall 122 toward the outlet port 132. The circle about which the bumps 158a,b,c are arrayed is spaced from the side walls of the chamber 102 to leave an unobstructed peripheral band 159 surrounding the bumps. A first bump 158a is preferably located adjacent and radially inward from the outlet port 132, while the other two bumps 158b, 158c are located approximately 120° about the circle from the first and on both sides of the inlet port 130. This arrangement provides a tripod support for the piston 110 and minimizes obstruction to flushing fluid flow. Preferably, the bumps are rounded in cross-section, although other shapes may be substituted. Moreover, and as will be clear below in the description of the reservoir operation, a single bump may suffice for the spacing purpose.

Plunger

FIGS. 8a and 8b shows the plunger assembly 104 including the plunger 106 which comprises, as seen in detail in FIGS. 9a–d, a relatively thin, elongated stem 160 terminating at an upper end in a top plate 162 whose upper surface forms a thumb rest 164, and at a lower end in a push rod 168. The stem 160 is preferably formed as a cross shape in horizontal section (FIG. 9d) with four radially directed walls 166a–d, although other configurations may be utilized. The cross-shape is preferred for preventing rotation of the plunger 106 in a similarly shaped aperture 170 (FIG. 10a) in the cap 108, and also to provide for a number of separate cantilevered fingers formed in one or more of the four walls 166 for cooperation with other components of the plunger assembly 104 and reservoir body 100.

For example, looking at the upper end of the plunger 106, one wall 166a of the cross-shaped stem 160 comprises a plunger release lever 172 defining a gap 174 with the main body of the stem 160. More particularly, the plunger release lever 172 extends outwardly from a first location 176 approximately 1 inch (2.5 cm) below the top plate 162. The release lever 172 continues upward and gradually angles outwardly from the remaining portion of the stem 160, thus defining the gap 174. At an upper end, the lever 172 defines an outwardly extending plunger trigger 180 adjacent a plurality of traction nubs 182. Just below the traction nubs 182, a recess 184 facing outwardly from the lever 172 is provided which terminates in a lower detent 186. The release lever 172 then continues downward from the detent 186 in a substantially constant line until joining with the main vertical profile of the stem 160.

The plunger release lever 172 is provided on one of the four walls 166 of the cross-shaped stem 160, and preferably compliments a cantilevered retraction stop 188 formed on the same wall. Those of skill in the art will recognize that the retraction stop 188 may be formed on one of the other walls, or more than one wall. The retraction stop 188 begins at a point approximately 2 inches (5.1 cm) below the top plate 162 and continues downward forming a cantilevered finger diverging from the main portion of the stem 160 across a gap 190. The outer edge of the retraction stop is preferably vertical and continuous with the remaining portion of the stem 160, and includes an outwardly projection tooth 192 at the lower end.

Just below the retraction stop 188, a pair of piston latches 194 are formed in opposing walls of the cross-shaped stem 160. The piston latches 194 again comprise cantilevered fingers depending downwardly from the walls and terminating in outwardly facing barbs 196. Preferably, the barbs 196 have an angled upper surface, although a perpendicular surface is shown. The piston latches 194 are preferably formed as extensions of two opposing walls 166a, 166c of the four defining the cross-shaped stem 160, and more particularly one of the piston latches comprises a projection of the wall 166a including the plunger release lever 172 and retraction stop 188. The plunger 106 continues downward from the piston latches 194 in the two opposing walls perpendicular to the piston latches 194 to terminate in lower comers 200. A pair of outwardly projection flanges 202 are provided at the level of the comers 200 and in the same plane as the walls 166a,c in which the piston latches 194 are formed. Finally, the plunger 106 continues downward from the flanges 202 in the centered push rod 168. The functions of the various elements of the plunger will be described below in conjunction with the other components of the reservoir 80.

Cap

Figure 10B:
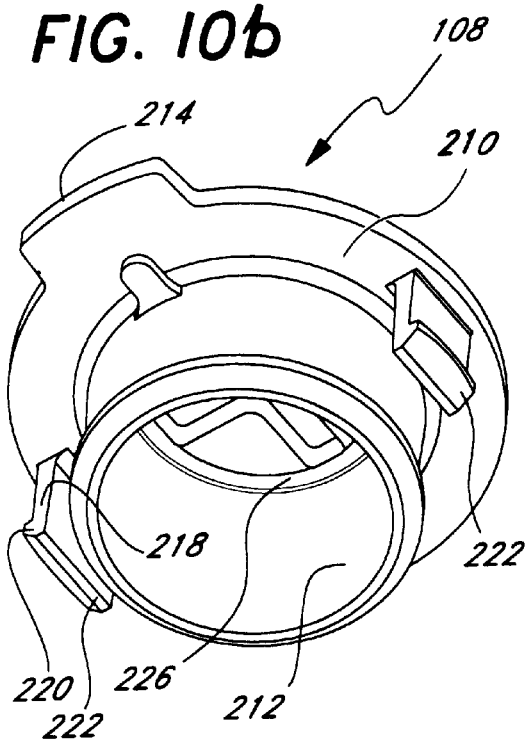
FIGS. 10a and 10b are top and bottom perspective views of a cap component of the reservoir of FIGS. 4 and 5.
Figure 10A:
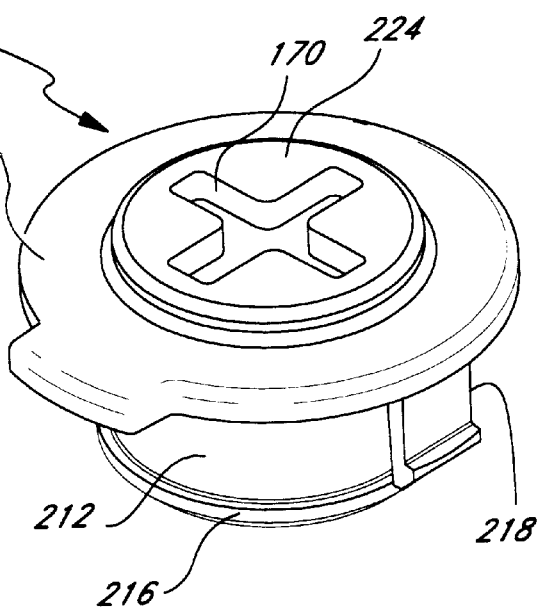

One of the other components of the plunger assembly 104, seen in detail in FIGS. 10a and 10b, comprises the cap 108 for attaching to the open mouth 124 of the body 100. The cap 108 comprises a circular top wall 210 having an integrally formed down tube 212 depending therefrom. The circularity of the top wall 210 is broken by an outwardly extending orientation tab 214. The down tube 212 continues and terminates in an outwardly projecting circular rib 216. A pair of diametrically opposed lock flanges 218 extend downward from a lower edge of the top wall 210. The lock flanges 218 comprise cantilevered fingers which terminate at outwardly projecting ledges 220 having lower cam surfaces 222. The aforementioned cross-shaped plunger aperture 170 is formed in a raised portion 224 of the top wall 210. The undersurface of the raised portion 224 at its intersections with the outwardmost portions of the cross-shaped plunger aperture 170 comprises a slightly undercut lock rim 226. The lock rim 226 is adapted to mate with both the plunger release lever 172, and the retraction stop 188, as will be described further below.

Piston

Figure 11B:
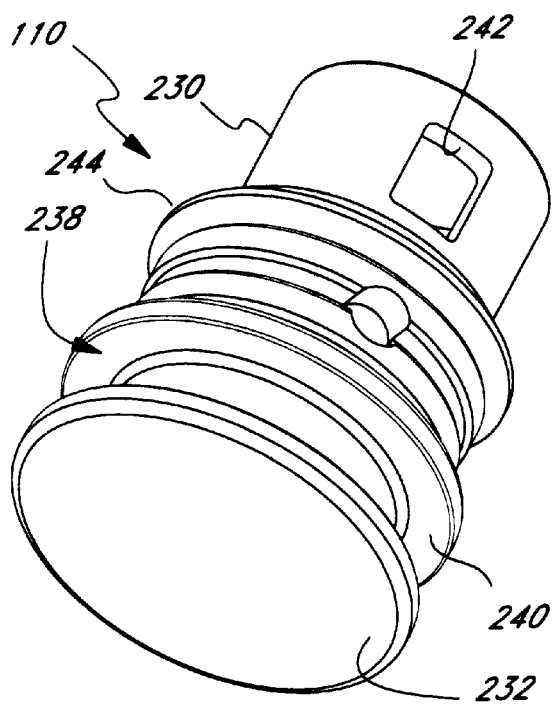
FIGS. 11a and 11b are top and bottom perspective views of a piston component of the reservoir of FIGS. 4 and 5.
Figure 11A:
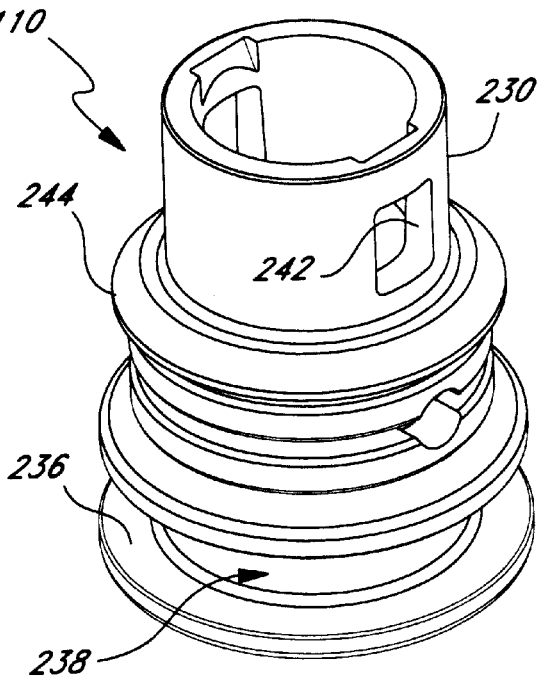

The piston 110 is seen in detail in FIGS. 11a and 11b and comprises a tubular body 230 extending upward from a planar, circular bottom wall 232. The entire piston is about 0.86 inch (2.18 cm) in axial height. The lower surface of the bottom wall 232 is preferably smooth and contacts the bumps 158 projecting upward from the reservoir bottom wall 122. The function of the bumps 158 is to space the piston 110 from the bottom wall, and in this regard, those of skill in the art will recognize that, in the alternative, bumps may be formed on the bottom face of the piston 110 rather than on the reservoir bottom wall 122. In addition, other piston/chamber configurations may be substituted, such as a convex or hemispherical piston bottom wall 232 interacting with a concave or hemispherical bottom wall 122.

The bottom wall 232 projects radially outwardly from the tubular body 230 and defines a lower wall 236 of a groove 238, which is completed by an upper wall 240. The groove 238 receives the annular seal 112. An upper portion of the tubular body 230 is interrupted by a pair of diametrically opposed latch apertures 242. The latch apertures 242 are sized to receive the barbs 196 of the piston latches 194. In this manner, the plunger 106 and piston 110 are coupled. Preferably, the latch apertures 242 are undercut at an angle to receive the preferably angled barbs 196 in a more secure coupling, although the interacting surfaces are shown in the drawings perpendicular to the plunger axis. One or more circular ribs 244 are provided above the groove 238 for retaining the contamination shield 116. Finally, an upstanding guide tube 246 (FIG. 12a) is rigidly formed with the bottom wall and extends upward concentrically within the tubular body 230 approximately 0.23 inch (0.58 cm).

Reservoir Bracket

Referring back to FIGS. 4 and 5, the bracket 87 may be made of molded ABS (acrylo-nitryle-butadiene-styrene) and comprises a lower reservoir retaining portion 250, a rear mounting plate 252, and an upper plunger operating arm 254. The planar mounting plate 252 includes a pair of elongated vertical slots 256. A pair of arcuate, resilient retaining arms 258 extend forward from the mounting plate 252 and are attached thereto via a bridge portion 260. The retaining arms 258 are cylindrical in cross-section and terminate at opposing vertical edges 262 so that the retaining arms 258 define a partial cylinder of approximately 270°. The diameter of the partial cylinder circumscribed by the retaining arms 258 is approximately the same, and preferably slightly less than, the outer diameter of the cylindrical body 100 of the reservoir 80. More particularly, the cylindrical body 100 preferably has an outer diameter of approximately 0.89 inch (2.26 cm), and the inner diameter of the partial cylinder defined by the retaining arms 258 is approximately 0.86 inch (2.18 cm). In addition, the edges 262 are spaced approximate 0.72 inch (1.83 cm) apart so that the cylindrical body 100 may be pressed therebetween and into engagement with the resilient retaining arms 258 to be held securely thereto.

At the top edge of the partial cylinder defined by the retaining arms 258, the bracket 87 includes a cavity 264 continuing through the mounting plate 252. Above the cavity 264, the plunger operating arm 254 is integrally formed with the mounting plate 252 at a horizontal wall 266, and includes a pair of reinforcing side walls 268 extending upward therefrom. The sidewalls are joined at their front edges by a concave, vertical front wall 270. At the top of the front wall 270, a reinforcing spar 272 supports an upper thumb rest 274. The thumb rest 274 extends substantially perpendicularly to the arcuate front wall 270. Finally, a pair of stop flanges 276 extend forwardly from the lower end of the front wall 270. The stop flanges 276 cooperate with the reservoir 80, as will be described below.

Reservoir/Bracket Assembly

A preferred orientation of the reservoir 80 assembled to the bracket 87 is shown in FIGS. 4 and 5, with the mounting plate 252 in a vertical plane at the back side of the assembly. The reservoir retaining arms 258 thus extend forwardly and accept the body 100 with the tabs 127 resting on the upper edges of the arms to prevent relative downward movement of the reservoir in the bracket 87. Reservoir 80 is positioned in the bracket 87 so that the opposed wings 126 extend forward and backward, respectively. The rear wing 126 extends within the cavity 264 in the bracket 87 to provide a convenient means for orienting the reservoir 80. This orientation also displays the volumetric markings 120 to the front, and the valve 152 of the stopcock 78 faces forward. Furthermore, the plunger release lever 172 faces forward, so that the plunger trigger 180 is conveniently disposed for actuation of the plunger assembly 104. Alternatively, the wings 126 are at the same elevation as the lower edges of the tabs 127 and thus can provide the same stop function of the tabs in preventing relative movement of the reservoir 80 with respect to the retaining arms 258, at least in one direction. Thus, if necessary, the reservoir 80 can be turned at a variety of angles about the reservoir axis with respect to the illustrated orientation.

Reservoir Assembly

The assembled reservoir 80 is seen in FIGS. 4 and 5, and also in cross-section in FIGS. 12 and 13. The cap 108 is preferably secured to the open mouth 124 of the body 100 by engagement between the lock flanges 218 and the slots 125. Prior to engaging the cap 108 on the body 100, the plunger 106 is inserted into the crossed aperture 170 in the raised portion 224. The lower end of the plunger 106 is then coupled to the upper end of the piston 110. In coupling the plunger 106 and piston 110 the spring 114 resides concentrically within the tubular body 230 of the piston, and outside of the guide tube 246. As shown in the figures, the piston latches 194 cam inwardly past the upper end of the tubular body 230 and spring outward into the latch apertures 242 to secure the two components while allowing some axial play therebetween.

FIGS. 12a and 12b show the plunger assembly 104 in a fully inserted position within the reservoir body 100. In this position, the plunger release lever 172 is resiliently biased outward against one of the arms of the plunger aperture 170 with the edge of the raised portion 224 extending within the recess 184, and the detent 186 catching on the undercut corner of the raised portion. The contamination shield 116 is shown extended surrounding the plunger stem 160 and connected between the down tube 212 of the cap 108 and the outwardly projection rib 244 on the piston tubular body 230. A pair of elastomeric retaining rings 280 secure the contamination shield against the rib 216 of the cap 108 and the rib 244 of the piston 110. The contamination shield 116 is preferably a polyethylene tube having a non-corrugated cross-section which is flexible and will collapse when the plunger assembly 104 is retracted from the body 100.

When the bumps 158 contact the bottom wall 232 of the piston 110 a gap G is formed between the piston and reservoir bottom wall 122. This gap G remains open constantly and provides a passageway for flushing fluid. The gap G is determined by the axial height of the bumps 158, and is preferably between about 0.005 inches and 0.030 inches (0.127–0.762 mm), and more preferably about 0.014 inch (0.356 mm). This small space provides for sufficient flow of flushing fluid, while minimizing the fluid volume needed for flushing the reservoir 80 between sampling sequences. The positioning of the inlet port 130 and outlet port 132 also enhance the flushing action, as seen in FIG. 6b. The inlet flow of flushing fluid is shown as outwardly directed arrows 228 from the inlet port 130. This flow effectively flushes the thin volume under the piston 110, and the bumps 158 are designed to minimize structure within the volume which might interrupt or stagnate this flow.

A space S shown in FIG. 12a represents the effective relative axial travel available between the plunger 106 and piston 110. In this state, the release lever detent 186 engages and is biased upward against the cap 108 to define a first position of the plunger 106 with the piston 110 bottomed out within the chamber 102. The spring 114 is compressed between the corners 200 and outwardly extending flanges 202 and the lower wall 236, thus biasing the plunger 106 and piston 110 apart. Because the piston 110 is bottomed out, the spring 114 also biases the plunger upward, at least initially, with respect to the body 100. The piston latches 194 and apertures 242 limit the upward travel of the plunger 106 relative to the piston 110. When released, the plunger 106 will move upward relative to the piston 110 over the space S until the piston latch barbs 196 and apertures 242 engage, at which time the two components move upward in tandem. The space S is nominally about 0.025 inch (0.635 mm). It should be noted that in the position shown in FIGS. 12a–c, the plunger 106 is not completely bottomed out within the guide tube 246, and the plunger could be depressed a small axial distance farther, as indicated by the space underneath the push rod 168. Thus, S is only the effective axial travel distance between the plunger 106 and piston 110 when the plunger is being retracted.

Operation

In use, the reservoir 80 is connected in the sampling system 70 line as shown in FIG. 3 before or after positioning on a support post or attaching to the patient's arm, for example. In this regard, the rear mounting plate 252 of the bracket 87 is normally inserted in a tongue-and-groove fashion into complimentary structure provided on an upstanding hospital support post. The bracket 87 can thus be attached to a portable stanchion or other such post adjacent the patient and at a convenient, elevated position for the nurse or clinician. The reservoir 80 is typically positioned in an inverted vertical orientation, with the bottom wall 122 actually above the open mouth 124. In this manner, the numeric markings corresponding to the gradations 120 are displayed upright and increase in value from top to bottom. The reservoir 80 and bracket 87 may also be attached to the patient's arm with a strap through the elongated vertical slots 256, looped around the arm and secured with Velcro or other such expedient. In either mounting location, the reservoir 80 may be held by the retaining arms 258 with the wings 126 aligned toward and away from the bracket 87, as shown in the drawings, or sideways thereto. Thus, if necessary the reservoir 80 can be turned sideways in its mount to accommodate different CCU or operating room layouts. Finally, the reservoir 80 can be removed completely from the bracket 87 and operated in a conventional two-handed manner. This flexibility is previously unavailable in blood sampling reservoir designs.

Prior to drawing a blood sample, the plunger assembly 104 is in the position shown in FIGS. 12a–d with the plunger release lever 172 locking the assembly within the body 100. The gap G allows flushing fluid through the second tubing line 82 to pass into the inlet port 130 and underneath the piston 110 to exit the volume within the reservoir 80 through the outlet port 132. The flushing fluid clears out residual blood from the reservoir 80 thus preventing clotting or other such undesirable consequences of static blood. With the orientation of the inlet port 130, the fluid enters the gap G in a direction perpendicular to the piston 110 which causes it to immediately fan or splay out radially in a thin sheet. FIG. 6b illustrates the preferred flow vectors 228 of the fluid entering the gap G from the inlet port 130. The position of the inlet port 130 enhances the flushing effect as portions of the sheet of fluid are directed to the peripheral wall of the chamber 102, while some is directed toward the outlet port 132. As seen in FIG. 12c, the gap G is relatively constant between the piston 110 and bottom wall 122 except for a peripheral channel 284 created above the unobstructed peripheral band 159 surrounding the bumps 158. This channel 284 is formed by the circumferential termination of the bottom wall 232 of the piston 110 and the relief space formed by the stepped lower edge of the seal 112 prior to the first wiper of the seal. The flushing fluid not directed to the outlet port 132 enters the peripheral channel 284 and continues circumferentially around the chamber 102 toward the outlet port 132. The outlet port 132 opens to the peripheral channel 284 and thus efficiently drains the circumferentially flowing fluid from the channel as well as the fluid coming more directly from the inlet port 130. Moreover, the bumps 158 are relatively small and thus a minimum amount of flushing fluid is needed to maintain patency of the reservoir 80.

Because the flushing fluid continues along the first tubing line 74 past the sampling sites 98a and 98b and into the patient, a minimum of fluid is desired to avoid overdilution of the patient's blood stream. In designing the proper sized gap G, a number of factors should be taken into account, such as the diameter of the reservoir body 100, the flow rate and pressure of the flushing fluid, the inlet port 130 size, the time period that the reservoir will be connected in the pressure monitoring system, etc. Desirably, under preferred operating conditions, the gap G is such that a 360° thin sheet of fluid is directed from the inlet port 130 toward the peripheral wall of the chamber 102 and into the channel 284. In one exemplary embodiment, the gap G is less than the inlet port 130 orifice, which is about 0.07 inch (1.78 mm), but is more desirably between about 0.005 inches and 0.030 inches (0.127–0.762 mm) for a reservoir 80 having a chamber inner diameter of about 0.77 inch (1.97 cm). The inlet fluid pressure range will be determined by the operating specifications of the pressure transducer 90, and is typically no more than 300 mm Hg, and desirably about 250 mm Hg. As mentioned, this pressure is generated by an inflatable bag surrounding the fluid supply bag. The flow rate of flush fluid through the system 70 between blood samples is typically between 50–100 cc/minute.

When a blood sample is to be taken, the flow of flushing or infusion fluid is halted, such as with the use of a stopcock valve (not shown) upstream of the reservoir 80. The nurse or clinician then grasps the reservoir 80 with one finger or thumb on the thumb rest 274 at the top of the bracket 87 and the other finger or thumb underneath the plunger trigger 180 of the plunger release lever 172. By squeezing the two surfaces together, the plunger release lever 172 pivots inward due to the gap 174. At some point, the detent 186 releases from the underside of the crossed plunger aperture 170, thus releasing the plunger assembly 104 to travel upwardly within the body 100. Thus, the one-handed squeezing operation simultaneously releases the plunger assembly 104 and commences its travel within the reservoir chamber 102.

The plunger assembly 104 is retracted from within the body 100 by continued squeezing pressure between the thumb rest 274 and the plunger trigger 180. The body 100 is restrained from upward movement by the stop flanges 276 on the bracket 87. The one-handed squeezing operation to retract the plunger assembly 104 is a major advantage of the present invention, and frees the clinician's other hand for attending to other patient needs. In addition, one need not brace the reservoir body 100 to retract the plunger assembly 104, as is normally the case with conventional pull-type syringe-like devices. Finally, the force needed to retract the plunger assembly 104 is the same as with the pull-type syringe device, but is easier to generate with a squeezing operation as opposed to a pulling operation. Therefore, nurses or clinicians with less strength can easily operate the reservoir 80.

The plunger assembly 104 may be retracted to withdraw a varied amount of fluid sufficient to pull pure blood past both of the sampling sites 98a and 98b. This volume differs in different hospital settings, but is typically 12 cc in an operating room environment and 5 cc in the CCU. The illustrated reservoir body 100, as described above, has a capacity of 12 cc when the plunger assembly 104 is fully retracted.

FIGS. 13a and 13b show the plunger assembly 104 in a second position fully retracted with respect to the reservoir body 100. In this position, the plunger release lever 172 is prevented from further retraction from the body 100 by the interference between the outwardly projecting tooth 192 of the retraction stop 188 and the undercut edge 226 (FIG. 12d) of the raised portion 224 of the cap 110. The total travel of the plunger 106 is shown as T in FIG. 12a, and is approximately 1.73 inches (4.39 cm) in the exemplary embodiment. This distance will vary depending on the volume drawn into the reservoir, and the diameter of the chamber 102, but the small distance is ergonomically designed to facilitate one-handed operation by clinicians of smaller features. Desirably, the distance T is no greater than the span of thumb and forefinger of the smallest clinician who may operate the system. The nurse or clinician is notified of the full retraction of the plunger assembly 104 by the positive interaction between the tooth and the cap 110. Of course, those of skill in the art will recognize that a number of stops can be provided for flexibility in withdrawing sequential fluid volumes through the first tubing line 74. The contamination shield 116 collapses when the plunger assembly 104 is fully retracted.

It will be noted that the seal 112 prevents blood and other fluid from traveling upward into the region within the body 100 and around the plunger assembly 104. To further protect against contaminating the blood within the body 100 below the piston 110, the contamination shield 116 separates the internal components of the plunger assembly 104 from the inner walls of the reservoir 100, which do come in contact with the volume of fluid eventually infused back into the patient.

After full retraction of the plunger assembly 104, the stopcock 78 is closed and samples of blood are taken at the sites 98a and 98b. This operation preferably takes place with a blunt-tipped cannula syringe, and is well described in the prior art. It should be noted, however, that a single sampling site may be used, and other sampling devices such as sharp-tipped cannulas may also be used, with less security for the nurse or clinician. After samples have been taken, the stopcock 78 is opened and the volume within the reservoir 80 is reinfused back into the patient. This is accomplished by depressing the plunger assembly 104 within the body 100. The nurse or clinician places a thumb or finger on the thumb rest 164 of the top plate 162, and the other digit on the same hand on the underside of the forwardly extending wing 126.

By squeezing the thumb and finger together, the plunger assembly 104 is displaced downward within the body 100. The plunger assembly 104 continues downward until the piston 110 contacts the bumps 158 on the bottom wall 122, at which point the piston 110 stops moving downward, but the plunger 106 continues. The spring 114 is compressed by the outwardly extending flanges 202 and lower wall 236 until the detent 186 on the plunger release lever 172 locks with the underside of the plunger aperture 170.

The provision of the spring 114 provides several advantages to the blood sampling system 70 of the present invention. First, the spring 114 biases the piston 110 downward into contact with the bumps 158 on the bottom wall 122. This insures a constant gap G for fluid to flow through the inlet port 130 to the outlet port 132 with the attendant flushing advantages described above. The spring 114 also eliminates the need for close manufacturing tolerances of the height of the components of the plunger assembly 104, which would otherwise be the case without the biased piston 110 and bumps 158. That is, the spring 114 enables the size range of the gap G to be determined solely by the tolerances associated with the bumps 158. Any tolerance stacking problems in the formation of the parts of the plunger assembly 104 is compensated for and covered up by the spring 114. Thus the parts can be made with loosened tolerances which reduces the manufacturing costs of the reservoir 80. Finally, the spring 114 provides a particular frequency response of the plunger assembly 104 so that pressure monitoring by the transducer 90 is optimized. That is, the length and character of tubing and sampling ports between the reservoir 80 and the patient determines a particular volume with the sampling system 70, and the spring constant of the spring 114 interacts with this volume, or fluid mass if you will, to affect the damping of the fluid system. This control of the damping factor is useful for optimizing the pressure measuring operation.

Figure 14:
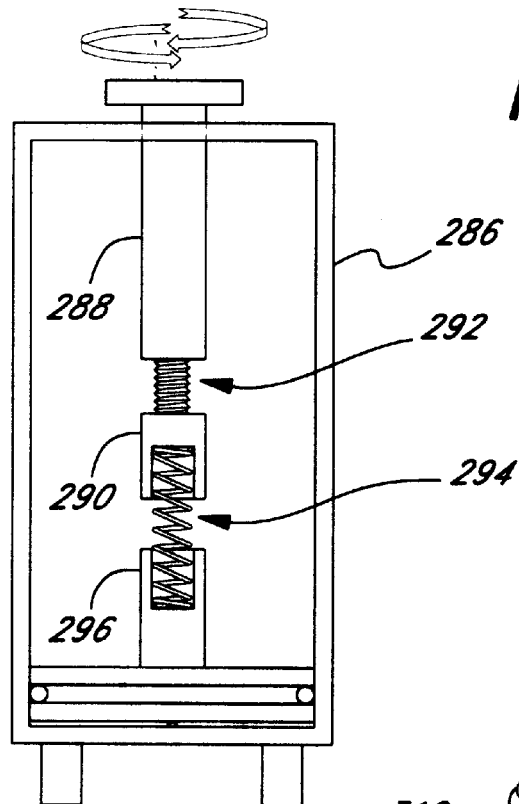
FIG. 14 is a schematic cross-sectional view of a sampling reservoir similar to that shown in FIGS. 4 and 5 with an adjustable piston spring load.

In a further embodiment of the present invention, schematically shown in FIG. 14, the spring rate of the spring 114 may be adjustable. In this embodiment, a reservoir 286 includes a plunger 288 which threadingly engages a spring yoke 290 via a threaded rod 292. A spring 294 is placed in compression between the yoke 292 and a piston 296. The relative position of the yoke 292 determines the pre-load on the spring 294, and thus the force required to raise the piston 296 when the plunger 288 is locked in the reservoir as before. This control enables the clinician to optimize dynamic response by performing a frequency response test and then adjusting the damping coefficient of the system if the frequency response is unsuitable.

FIG. 15 illustrates another one-handed reservoir 300 for use in a blood sampling system. The reservoir 300 comprises an outer housing 302 having an oval cross-section and a pair of opposed elongated slits 304 in the narrow sides. The slits receive outward extensions of an inner housing 306 also having an oval cross-section which is linearly reciprocal within the outer housing 302. The inner housing 306 includes an inner chamber (not shown) with an inlet port 308 and an outlet port 310 communicating therewith. A pair of thumb rings 312 rigidly attached to the inner housing 306 project outward through the slits 304. The functioning of the reservoir 300 is best described with respect to FIGS. 16*a*–*c* which illustrates an identical reservoir 314 except the rings 312 are replaced with flanges 316. Otherwise, like elements will receive like numbers.

As seen in FIGS. 16*a*–*c*, the reservoir 314 includes an upper cap 318 secured over an open upper end of the outer housing 302 with a piston 320 rigidly attached thereto and extending into a variable volume chamber 322 of the inner housing 306. A seal 324 seats on a distal end of the piston 320 and defines one end of the variable volume chamber 322 opposite the inlet and outlet ports 308, 310. A contamination shield 326 extends between an upper end of the inner housing 306 and the seal 324.

The reservoir 314 functions in a similar manner as the previously described reservoir 80, and is preferably installed in a pressure monitoring line with the inlet port 308 toward a pressure transducer and fluid supply, and the outlet port 310 toward the sampling sites and patient. FIG. 16*a* shows the inner housing 306 in a first position with respect to the outer housing 302 wherein the piston 320 is in contact with a bottom wall 328 of the chamber 322. Desirably, a small gap is maintained between the piston 320 and chamber bottom wall 328 to allow flow of a flushing fluid therethrough, as described previously. In this regard, protrusions may be formed on the piston 320 or chamber bottom wall 328 to form the gap. Also, the inlet port 308 is shown as before entering the chamber perpendicularly with respect to the bottom wall 328 and in a position spaced from the periphery to enhance the flushing effect. In contrast to the earlier embodiment, however, the outlet port 310 is still positioned at the periphery but is parallel to the chamber bottom wall 328.

FIG. 16*b* shows a second position of the inner housing 306 with respect to the outer housing 302 wherein the piston 320 is no longer in contact with the chamber bottom wall 328 and a volume of fluid 330 has been drawn into the chamber 322. The bottom wall 328 stops against a lower surface 331 of the outer housing 302. At this stage, the clinician closes a stopcock 332 and samples blood from one or more sites between the reservoir 314 and the patient. The reservoir 314 may include features such as a spring-loaded piston as previously described.

The reservoir 314 is distinguished from the reservoir 80 described previously by the lack of a bracket for mounting to a support pole or patient's arm. Of course, such structure could be provided for the reservoir 314 secured to the inner or outer housing. The one handed squeezing operation of the reservoir 314 is maintained, however, without a separable bracket. With reference to FIG. 16*a*, force arrows 334 show the location and movement of opposed thumb and fingers to move the inner housing 306 from its first position to its second position in FIG. 16*b*. Conversely, FIG. 16*b* illustrates force arrows 336 that opposed thumb and fingers apply to move the inner housing 306 from its second position to its first position.

It is understood that the examples and embodiments described herein and shown in the drawings represent only the presently preferred embodiments of the invention, and are not intended to exhaustively describe in detail all possible embodiments in which the invention may take physical form. Indeed, various modifications and additions may be made to such embodiments without departing from the spirit and scope of the invention. For example, although the present sampling system is described and is particularly useful for venous or arterial blood sampling, other bodily fluids such as urine may be sampled, and the device may have other uses such as in wound drainage.

What is claimed is:

1. A reservoir for use in a fluid sampling system, comprising:
   a reservoir body defining a chamber within;
   a piston having a piston wall facing the chamber and displaceable within the body from a first position to a second position to vary the volume of the chamber;

a fluid inlet port and a fluid outlet port open to the chamber;

structure on either the body or the piston which maintains a minimum gap between the piston wall and the body when the piston is in the first position, the gap defining a volume to which the inlet and outlet ports communicate to allow fluid to flow therebetween; and a biasing member which urges the piston wall into the first position.

2. The reservoir of claim 1, wherein the reservoir comprises a syringe-like device having an axis with the inlet port located at one axial end of the chamber and the piston being axially displaceable along the axis between the first and second positions.

3. The reservoir of claim 2, wherein the chamber is centered about the axis and the inlet port is located off-center in the one axial end.

4. The reservoir of claim 1, wherein the piston wall faces the inlet port and the inlet port is oriented substantially perpendicularly with respect to said piston wall.

5. The reservoir of claim 1, further including a plunger assembly reciprocal within the reservoir body comprising the piston on a first end and a plunger on a second end extending outside of the body, wherein the biasing member is positioned between and urges apart the piston and plunger.

6. The reservoir of claim 5, wherein the body and plunger assembly cooperate to form a syringe-like device with the plunger assembly reciprocal along an axis defined by the body, and wherein the biasing member acts substantially in the axial direction.

7. The reservoir of claim 6, wherein the plunger includes locking detents which cooperate with apertures in the piston to couple the plunger and piston together while allowing relative axial movement therebetween.

8. The reservoir of claim 7, further including complementary structure on the plunger and on the body which maintains the plunger in a retracted position urging the piston wall into the first position.

9. The reservoir of claim 8, further including a trigger on the plunger which releases the plunger from the retracted position.

10. The reservoir of claim 9, wherein the trigger comprises a cantilevered lever member biased outward against an edge when the plunger is in the retracted position, the edge being fixed with respect to the body, the lever member including a detent which interferes with the edge and maintains the plunger in the retracted position until the lever member is displaced inwardly.

11. The reservoir of claim 1, wherein the structure which maintains a minimum gap between the piston wall and the body when the piston is in the first position comprises a protrusion on the piston wall.

12. The reservoir of claim 1, wherein the structure which maintains a minimum gap between the piston wall and the body when the piston is in the first position comprises a protrusion on an inner wall of the body facing the piston wall.

13. The reservoir of claim 12, wherein there are three protrusions on the inner wall generally evenly distributed about a circle spaced from side walls of the chamber.

14. The reservoir of claim 1, wherein the inlet port is in fluid communication with a line leading from a fluid source, and the outlet port is in fluid communication with a line leading to a fluid system of a patient.

15. The reservoir of claim 1, wherein magnitude of the biasing member is adjustable.

16. The reservoir of claim 15, further including a plunger reciprocal within the reservoir body and coupled to the piston with axial play therebetween, wherein the biasing member is a spring positioned between and urging apart the piston and plunger.

17. A method of flushing a reservoir used in a fluid sampling system, comprising:

providing a reservoir having a chamber and a displaceable piston having a piston wall facing the chamber and displaceable within the body to vary the volume of the chamber;

connecting a proximal portion of tubing between a source of flushing fluid and an inlet to the variable volume chamber;

connecting a distal portion of tubing between a fluid system of a patient and an outlet to the variable volume chamber;

biasing the piston into a first position within the variable volume chamber with the piston wall adjacent the inlet and outlet ports; and maintaining a minimum gap between the piston wall and the chamber when the piston is in the first position with structure on either the chamber or the piston, the gap defining a volume to which the inlet and outlet ports communicate and allow fluid to flow from the proximal portion of tubing to the distal portion of tubing.

18. The method of claim 17, wherein the reservoir comprises a syringe-like device having an axis with the inlet port located at one axial end of the chamber and the method includes axially displacing the piston along the axis into the first position.

19. The method of claim 18, wherein the chamber is centered about the axis and the inlet port is located off-center in the one axial end, the method including flowing flushing fluid into the chamber through the inlet port when the piston is in the first position.

20. The method of claim 17, wherein the piston wall of the piston faces the inlet port and the inlet port is oriented substantially perpendicularly with respect to the piston wall, the method including flowing flushing fluid into the chamber through the inlet port when the piston is in the first position, wherein flushing fluid contacts the piston wall perpendicularly and fans out within the gap.

21. The method of claim 17, including a plunger reciprocal within the reservoir body and coupled to the piston with axial play therebetween, wherein the method includes adjusting the magnitude of the biasing member.

22. The method of claim 17, further including a plunger assembly reciprocal within the reservoir body comprising the piston on a first end and a plunger on a second end extending outside of the body, wherein the biasing member is positioned between and urges apart the piston and plunger, and wherein the body and plunger assembly cooperate to form a syringe-like device with the plunger assembly reciprocal along an axis defined by the body, the method including biasing the piston in the axial direction into the first position.

23. The method of claim 22, including coupling the plunger and piston together while allowing relative axial movement therebetween.

24. The method of claim 22, including maintaining the plunger in a retracted position urging the piston into the first position.

25. The method of claim 24, further including actuating a trigger on the plunger to release the plunger from the retracted position.

26. The method of claim 17, including maintaining the minimum gap between the piston wall and the body when the piston is in the first position with a protrusion on the piston wall.

27. The method of claim 17, including maintaining the minimum gap between the piston wall and the body when the piston is in the first position with a protrusion on an inner wall of the body facing the piston.

28. A reservoir for use in a fluid sampling system, comprising:
- a reservoir body defining a variable volume chamber within, the body having a peripheral wall and a bottom wall;
- a fluid inlet port extending perpendicularly through the bottom wall of the body and open to the chamber;
- a fluid outlet port open to the chamber;
- a piston displaceable within the body from a first position adjacent the bottom wall to a second position spaced farther away from the bottom wall to increase the volume of the chamber, the piston having a pressure surface which is spaced from the bottom wall to form a narrow gap therebetween when the piston is in the first position, the fluid inlet and outlet ports being open to the gap; and
- a seal surrounding the pressure surface and providing a fluid-tight seal between the piston against the peripheral wall of the chamber, wherein fluid entering the chamber through the inlet port when the piston is in the first position is directed generally in a 360° sheet across the bottom wall and toward the peripheral wall of the chamber.

29. The reservoir of claim 28, wherein the pressure surface is substantially flat and disposed parallel to the bottom wall.

30. The reservoir of claim 28, including a protrusion on the pressure surface which contacts the bottom wall and forms the gap.

31. The reservoir of claim 28, including a protrusion on the bottom wall surface which contacts the pressure surface and forms the gap.

32. The reservoir of claim 31, wherein there are three protrusions on the bottom wall generally evenly distributed about a circle spaced inwardly from peripheral wall.

33. The reservoir of claim 28, wherein the pressure surface is spaced between approximately 0.005 inches and 0.030 inches from the bottom wall when the piston is in the first position.

34. The reservoir of claim 28, wherein the fluid outlet port extends perpendicularly through the bottom wall of the body.

35. The reservoir of claim 28, wherein the inlet port is offset from the peripheral wall and the outlet port is adjacent the peripheral wall.

36. A method of sampling fluid from a human, comprising:
- providing a reservoir body defining a variable volume chamber within, the reservoir body having a peripheral wall and a bottom wall;
- connecting the chamber to a vessel of the human by connecting a first conduit to a fluid outlet port open to the chamber;
- connecting the chamber to a source of flushing solution by connecting a second conduit to a fluid inlet port extending perpendicularly through the bottom wall and offset from the peripheral wall;
- providing a piston displaceable within the reservoir body from a first position adjacent the bottom wall to a second position spaced farther away from the bottom wall to increase the volume of the chamber, the piston having a pressure surface facing the bottom wall and including a seal surrounding the pressure surface and providing a fluid-tight seal between the piston against the peripheral wall of the chamber; and
- flushing the chamber between the piston and the bottom wall such that fluid entering the chamber through the inlet port when the piston is in the first position is directed generally in a 360° sheet across the bottom wall and toward the peripheral wall of the chamber.

37. The method of claim 36, wherein the pressure surface is substantially flat and disposed parallel to the bottom wall.

38. The method of claim 36 wherein the fluid inlet port and fluid outlet port extend perpendicularly through the bottom wall and parallel to each other.

* * * * *